United States Patent
Basbas et al.

(10) Patent No.: US 8,481,726 B2
(45) Date of Patent: *Jul. 9, 2013

(54) PROCESS FOR THE PREPARATION OF STERICALLY HINDERED NITROXYL ETHERS

(75) Inventors: Abdel-Ilah Basbas, Basel (CH); Davide Alvisi, Bondeno (IT); Robert Cordova, Madison, WI (US); Michael Peter Difazio, Spanish Fort, AL (US); Walter Fischer, Reinach (CH); Joseph A. Kotrola, Mobile, AL (US); Tiziano Nocentini, Pistoia (IT); James Robbins, Satsuma, AL (US); Kai-Uwe Schöning, Oberwil (CH)

(73) Assignee: BASF SE, Ludwigshafen (DE)

( * ) Notice: Subject to any disclaimer, the term of this patent is extended or adjusted under 35 U.S.C. 154(b) by 551 days.

This patent is subject to a terminal disclaimer.

(21) Appl. No.: 12/308,595

(22) PCT Filed: Jun. 25, 2007

(86) PCT No.: PCT/EP2007/056301
§ 371 (c)(1),
(2), (4) Date: Mar. 18, 2011

(87) PCT Pub. No.: WO2008/003605
PCT Pub. Date: Jan. 10, 2008

(65) Prior Publication Data
US 2011/0160453 A1 Jun. 30, 2011

(30) Foreign Application Priority Data

Jul. 5, 2006 (EP) .................................. 06116619
Apr. 25, 2007 (EP) .................................. 07106899

(51) Int. Cl.
*C07D 211/94* (2006.01)
*C07D 401/12* (2006.01)
*C07D 401/14* (2006.01)
*C07D 403/12* (2006.01)
*C07D 403/14* (2006.01)
*C07B 43/00* (2006.01)

(52) U.S. Cl.
USPC ........... 544/198; 544/209; 546/184; 546/188; 546/189

(58) Field of Classification Search
USPC .................. 544/198, 209; 546/184, 188, 189
See application file for complete search history.

(56) References Cited

U.S. PATENT DOCUMENTS

| | | | | |
|---|---|---|---|---|
| 4,921,962 A | 5/1990 | Galbo et al. | ................ | 546/184 |
| 5,374,729 A | 12/1994 | Galbo | ................ | 546/242 |
| 2003/0171461 A1 | 9/2003 | Hafner et al. | ................ | 524/99 |
| 2005/0104042 A1 | 5/2005 | Frey et al. | ................ | 252/399 |
| 2007/0191516 A1 | 8/2007 | Grey et al. | ................ | 524/99 |

FOREIGN PATENT DOCUMENTS

| | | |
|---|---|---|
| GB | 2347928 | 9/2000 |
| WO | 2005/005388 | 1/2005 |

OTHER PUBLICATIONS

P. Carloni et al., J. Heterocyclic Chem., vol. 40, (2003), pp. 459-464.
M. Ivan et al., Photochemistry and Photobiology, vol. 78, No. 4, (2003), pp. 416-419.
D. Barton et al., Tetrahedron, vol. 52, No. 31, (1996), pp. 10301-10312.
T. Ren et al., Bull. Chem. Soc. Jpn., vol. 69, (1996), pp. 2935-2941.
C. Johnson et al., Anal. Chem., vol. 68, (1996), pp. 867-872.
T. Inokuchi et al., Tetrahedron Letters, vol. 36, No. 18, (1995), pp. 3223-3226.
A. Beckwith et al., J. Org. Chem., vol. 53 (1988), pp. 1632-1641.
M. Sibi et al., J. Am. Chem. Soc., vol. 129, Mar. 16, 2007, pp. 4124-4125.

*Primary Examiner* — Venkataraman Balasubramanian
(74) *Attorney, Agent, or Firm* — Tyler A. Stevenson

(57) ABSTRACT

The present invention relates to a novel process for the preparation of specific sterically hindered nitroxyl ethers from their corresponding sterically hindered nitroxyl radicals by reacting it with an aldehyde and a hydroperoxide. This nitroxyl ether formation may be carried out from different starting nitroxyl radicals, which are subsequently further reacted to the desired compounds. The compounds prepared by this process are effective as stabilizers for polymers against harmful effects of light, oxygen and/or heat and as flame-retardants for polymers.

10 Claims, No Drawings

PROCESS FOR THE PREPARATION OF STERICALLY HINDERED NITROXYL ETHERS

The present invention relates to a novel process for the preparation of specific sterically hindered nitroxyl ethers from their corresponding sterically hindered nitroxyl radicals by reacting the nitroxyl radicals with an aldehyde and a hydroperoxide. This nitroxyl ether formation may be carried out from different starting nitroxyl radicals, which are subsequently further reacted to the desired compounds. The compounds prepared by this process are effective as stabilizers for polymers against harmful effects of light, oxygen and/or heat and as flame-retardants for polymers.

The term sterically hindered nitroxyl radical used in the present invention is a synonym for the term sterically hindered nitroxide, which is also frequently used in the literature. Consequently the term sterically hindered nitroxyl ether used in the present invention is used as a synonym for sterically hindered nitroxide ether or sterically hindered alkoxyamine.

Since sterically hindered nitroxyl ethers are of considerable industrial interest, many attempts have been made to develop industrially applicable processes for their manufacture.

For example WO 01/92228 describes a process for the preparation of nitroxyl ethers, e.g. N-hydrocarbyloxy substituted hindered amine compounds, by the reaction of the corresponding N-oxyl intermediate with a hydrocarbon in the presence of an organic hydroperoxide and a copper catalyst.

WO 03/045919 describes a process for the preparation of nitroxyl ethers, e.g. N-hydrocarbyl-oxy substituted hindered amine compounds, by the reaction of the corresponding N-oxyl intermediate with a hydrocarbon in the presence of an organic hydroperoxide and an iodide catalyst.

Reactions of 2,2,6,6-tetramethyl-1-oxopiperidinium chloride with ketones bearing an α-H atom are for example described by T. Ren et al. in Bull. Chem. Soc. Jpn., 69, 2935-2941 (1996) and by Y.-C. Liu et al. in Chinese Journal of Chemistry, 14(3), 252-258 (1996).

Surprisingly it has been found that sterically hindered nitroxyl ethers can be prepared by reacting a sterically hindered nitroxyl compound with an aldehyde in the presence of a hydroperoxide and a metal catalyst.

Very high yields are achieved in short reaction times. Additionally, the starting material concentration can be chosen very high, thus leading to an excellent volume/time yield. Reaction conditions are mild as compared to other prior art processes and the reaction is very selective without concomitant formation of dimeric, trimeric or oligomeric by-products.

One aspect of the invention is a process for the preparation of a sterically hindered nitroxyl ether of formula (I) or (II)

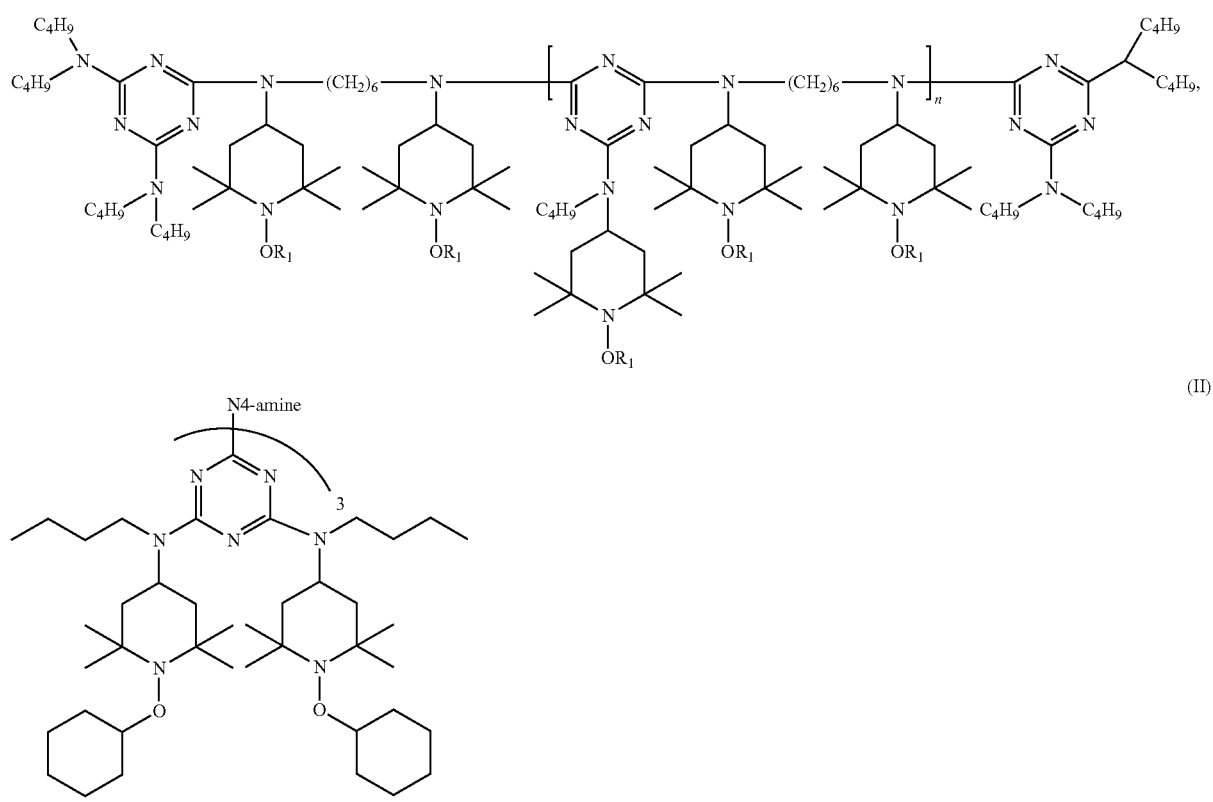

wherein N4-amine is

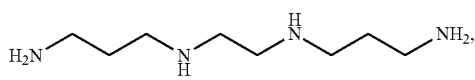 [SMILES: NCCCNCCNCCCN]

n is a number from 1 to 10 and $R_1$ is $C_1$-$C_5$alkyl;

which comprises in the case of the sterically hindered nitroxyl ether of formula (I) the steps a) reacting a compound of formula (Ia)

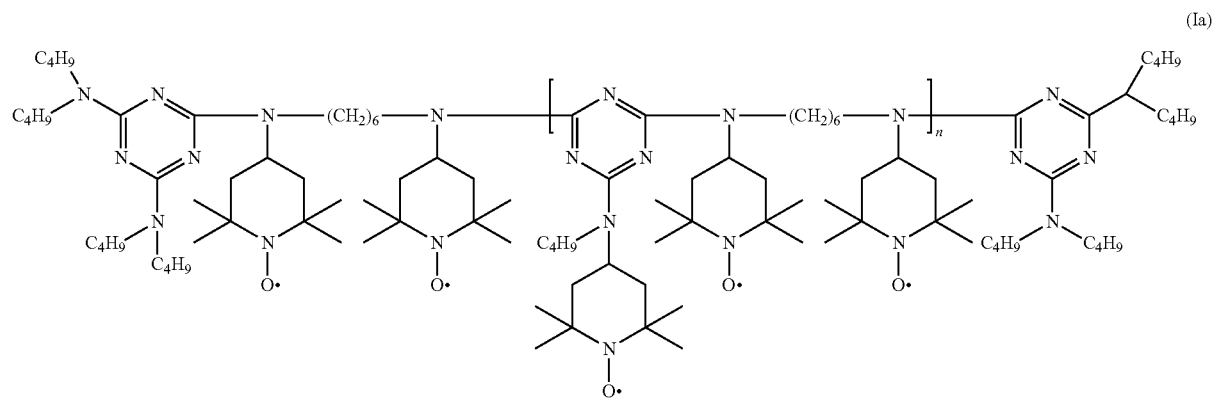

with n-hexylaldehyde, n-pentylaldehyde, n-butyraldehyde, n-propylaldehyde or acetaldehyde and a hydroperoxide in the presence of a metal catalyst; or b1) reacting a compound of formula (Ib)

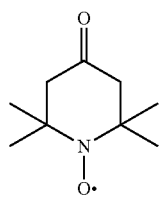

with n-hexylaldehyde, n-pentylaldehyde, n-butyraldehyde, n-propylaldehyde or acetaldehyde or a mixture of said aldehydes with their respective alcohols and a hydroperoxide in the presence of a metal catalyst to yield a compound of formula (Ic)

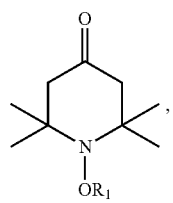

which is further reacted to form a compound of formula (I); which comprises in the case of the sterically hindered nitroxyl ether of formula (II)

a) reacting a compound of formula (IIa) or (IIb)

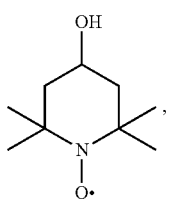

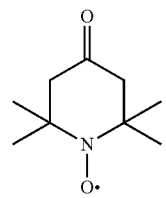

with a compound of formula (100) or (200)

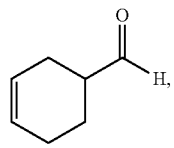

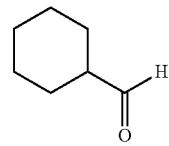

and a hydroperoxide in the presence of a metal catalyst to yield a compound of formula (IIc), (IId), (IIe) or (IIf)

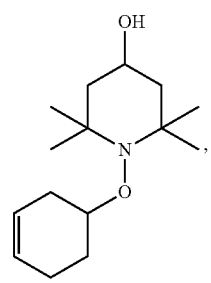

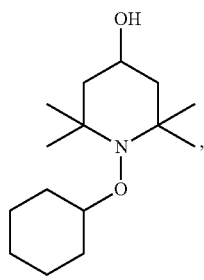
(IId)

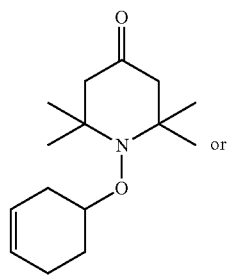
(IIe)

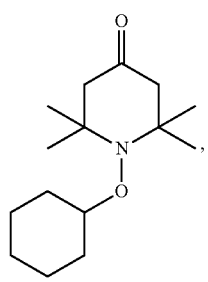
(IIf)

which are further reacted to form a compound of formula (II).

Preferably $R_1$ in formula (I) is n-propyl and the aldehyde is butyraldehyde.

Preferably in the compounds of formula (I) and (Ia) n is a mixture of the numbers 1, 3, 5 and 7.

For instance the hydroperoxide is of formula (II)

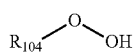
(II)

wherein $R_{104}$ is hydrogen, $C_5$-$C_{12}$cycloalkyl, $C_1$-$C_{24}$alkyl, phenyl or phenyl substituted by 1-4 alkyl $C_1$-$C_4$alkyl groups.

Preferably the hydroperoxide is tert. butyl hydroperoxide, cumyl hydroperoxide or $H_2O_2$.

Particularly preferred is $H_2O_2$.

The hydroperoxide and in particular $H_2O_2$ is typically dissolved in water and may be used in a concentration from 1% to 90% by weight based on the weight of the total solution. Preferably the concentration is between 20% and 70% by weight.

The hydroperoxide and in particular $H_2O_2$ can also be prepared in situ, for example by electrolysis.

The metal catalyst can be chosen from the group of transition metal catalysts or from the group of metal catalysts with Lewis-Acid character or of the group of water soluble ionic compounds and is preferably selected from the group consisting of scandium, titanium, vanadium, chromium, manganese, iron, cobalt, nickel, copper, zinc, gallium, germanium, yttrium, zirconium, niobium, molybdenum, ruthenium, rhodium, palladium, silver, cadmium, indium, tin, antimony, lanthanum, cerium, hafnium, tantalum, tungsten, rhenium, osmium, iridium, platinum, gold, mercury, thallium, lead, bismuth, aluminum, magnesium, calcium, lithium, barium, boron, sodium, potassium, cesium, strontium or combinations thereof.

The metal catalyst can be bound to an organic or inorganic polymer backbone, providing a homogenous or heterogeneous catalytic system.

The metal catalyst mentioned above may contain anionic ligands commonly known in complex chemistry of transition metals, such as anions derived from inorganic or organic acids, examples being halides, e.g. $F^-$, $Cl^-$, $B^-$ or $I^-$, fluoro complexes of the type $BF_4^-$, $PF_6^-$, $SbF_6^-$ or $AsF_6^-$, anions of oxygen acids, alcoholates or anions of cyclopentadiene or oxides.

Further examples are: sulfate, phosphate, perchlorate, perbromate, periodate, antimonate, arsenate, nitrate, carbonate, the anion of a $C_1$-$C_{30}$carboxylic acid, such as formate, acetate, trifluoroacetate, trichloroacetate, propionate, butyrate, benzoate, stearate, phenylacetate, mono-, di- or trichloro- or -fluoroacetate, sulfonates, for example methylsulfonate, ethylsulfonate, propylsulfonate, butylsulfonate, trifluoromethylsulfonate(triflate), unsubstituted or $C_1$-$C_4$alkyl-, $C_1$-$C_4$alkoxy- or halo-, especially fluoro-, chloro- or bromo-substituted phenylsulfonate or benzylsulfonate, carboxylates, for example tosylate, mesylate, brosylate, p-methoxy- or p-ethoxyphenylsulfonate, pentafluorophenylsulfonate or 2,4,6-triisopropylsulfonate, phosphonates, for example methylphosphonate, ethylphosphonate, propylphosphonate, butylphosphonate, phenylphosphonate, p-methylphenylphosphonate or benzylphosphonate, and also $C_1$-$C_{12}$-alcoholates, such as straight chain or branched $C_1$-$C_{12}$-alcoholates, e.g. methanolate or ethanolate.

Anionic and neutral ligands may also be present up to the preferred coordination number of the complex cation of the metal catalyst, especially four, five or six. Additional negative charges are counterbalanced by cations, especially monovalent cations such as $Na^+$, $K^+$, $NH_4^+$ or $(C_1$-$C_4$ alkyl$)_4N^+$. These anionic and neutral ligands may be applied to adjust the reactivity of the corresponding transition metal, e.g. in order to diminish the catalyst activity.

The neutral ligands are commonly known in complex chemistry of transition metals. Suitable inorganic ligands are selected from the group consisting of aquo ($H_2O$), amino, nitrogen, carbon monoxide and nitrosyl. Suitable organic ligands are selected from the group consisting of phosphines, e.g. $(C_6H_5)_3P$, $(i$-$C_3H_7)_3P$, $(C_5H_9)_3P$ or $(C_6H_{11})_3P$, di-, tri-, tetra- and hydroxyamines, such as ethylenediamine, ethylenediamiotetraacetate (EDTA), N,N-dimethyl-N',N'-bis(2-dimethylaminoethyl)-ethylenediamine ($Me_6$TREN), catechol, N,N'-dimethyl-1,2-benzenediamine, 2-(methylamino) phenol, 3-(methylamino)-2-butanol or N,N'-bis(1,1-dimethylethyl)-1,2-ethanediamine, N,N,N',N'',N''-pentamethylenediethyltriamine (PMDETA), $C_1$-$C_8$-glycols or glycerides, e.g. ethylene or propylene glycol or derivatives thereof, e.g. di-, tri- or tetraglyme, and monodentate or bidentate heterocyclic $e^-$ donor ligands.

The metal catalyst, in particular the transition metal catalyst can further contain heterocyclic $e^-$ donor ligands which are derived, for example, from unsubstituted or substituted heteroarenes from the group consisting of furan, thiophene, pyrrole, pyridine, bis-pyridine, picolylimine, phenanthroline, pyrimidine, bis-pyrimidine, pyrazine, indole, salen, coumarone, thionaphthene, carbazole, dibenzofuran, dibenzothiophene, pyrazole, imidazole, benzimidazole, oxazole, thiazole, bis-thiazole, isoxazole, isothiazole, quinoline, bis-quinoline, isoquinoline, bis-isoquinoline, acridine, chromene, phenazine, phenoxazine, phenothiazine, triazine, thianthrene, purine, bis-imidazole and bis-oxazole.

For example the metal catalyst is a salt or a complex of Ag, Mn, Fe, Cu, Zr, Na, Mg, Ca, Al, Pd, In or Ce in any oxidation state.

For instance the metal catalyst is a salt or a complex of Fe, Cu, Mn, Na, Mg, Pd, In, Zr or Bi in any oxidation state.

Preferably the metal catalyst is a $Fe^{2+}$ or $Fe^{3+}$, a $Cu^+$ or $Cu^{2+}$, a $Na^+$ or a $Ca^{2+}$ salt.

Typical counter ions for the above metal ions are derived from inorganic or organic acids. Examples for counter ions are $Cl^+$, $NO_3^-$, $SO_4^{2-}$, $CO_3^{2-}$, $PO_4^{3-}$, $CH_3COO^-$, $SO_3^{2-}$ or $CF_3SO_3^-$.

The metal catalyst is typically present in an amount of 0.0005 to 10.0 molar equivalents, dependent on the metal. $Cu^+$ or $Cu^{2+}$, for instance, is preferably used in amounts of 0.0005 to 0.2 molar equivalents and more preferably from 0.005 to 0.05 molar equivalents, based on the molar equivalents of the sterically hindered nitroxyl radical. $Na^+$, for instance, is preferably used in amounts from 0.005 to 3.0 molar equivalents and more preferably from 0.01 to 2.0 molar equivalents, based on the molar equivalents of the sterically hindered nitroxyl radical.

The process is typically carried out at normal atmospheric pressure. In the case of aldehydes with very low boiling points, it may be advantageous to apply pressure during the reaction.

The reaction time is usually short, depending on the sterically hindered nitroxyl radical used. For example the reaction time varies from 0.5 hours to 20 hours, for instance it is from 1 hour to 7 hours.

The reaction is typically carried out at a temperature between 0° and 100° C. depending on the catalyst used.

For instance, if $Cu^+$ or $Cu^{2+}$ is used, the reaction temperature is in particular between 10° and 60° C. and preferably between 25° and 50° C. If $Na^+$ is used, the reaction temperature is preferably between 25° and 100° C., more preferably between 60° and 100° C.

The pH value may vary from 1 to 10. Preferably it is neutral to slightly acidic, for instance pH 4 to 6.

A variety of inorganic and organic acids may be used to keep the pH value in the preferred range, examples for inorganic and organic acids have already been mentioned above. Typical examples are HCl, $H_2SO_4$, $H_3PO_4$, $CH_3COOH$, $CH_3SO_3H$ or buffer systems based, for example, on $H_3PO_4$ or $CH_3COOH$.

The reaction can be carried out with or without additional solvents. In some cases it may be of advantage when the reaction is carried out in a two phase system, for instance one phase being water. Two phase systems may also prevail in those cases, where the aldehyde is not completely soluble in the aqueous phase. The sterically hindered nitroxyl radical may be either in the aqueous phase or in the organic phase and the aldehyde in the respective other phase. In the case of immiscible phases, it may be advantageous to apply either a phase transfer catalyst, typically an amphiphilic molecule, or a suitable inert cosolvent. Typical phase transfer catalysts are salts containing anions, such as halides, hydroxides, hydrogensulfates, phosphates of tetraalkylammonium and alkyl arylphosphonium compounds. Current examples of phase transfer processes can be found, for example, in the Chemical Industry Digest (2005), 18(7), 49-62, Topics in Catalysis (2004), 29(3-4), 145-161 or in Interfacial Catalysis (2003), 159-201.

Typical inert solvents are for example, water, alkanes, toluene, xylene, nitrobenzene, acetic acid, esters such as ethyl acetate, alcohols such as ethanol or tert-butanol, halogenated solvents such as methylene chloride or chlorobenzene, ionic liquids, ethers such as tetrahydrofuran or tert.-butylmethylether, NMP or supercritical carbon dioxide. Basically, all hydroperoxide-stable (e.g. hydrogen peroxide stable) solvents may be used in this process. As mentioned before alcohols may be used as co-solvents in the present process, in particular those which form the employed aldehyde upon oxidation. For instance, ethanol can be used in such processes, where the radical-forming species is acetaldehyde.

The aldehyde and the hydroperoxide can be used in a wide concentration range. They are typically used in an excess amount, compared to the sterically hindered nitroxyl radical. Typically for the aldehyde is an excess of 1.05 to 20 mol equivalents, for example 1.25 to 5 mol equivalents, based on the molar amount of the sterically hindered nitroxyl radical. The hydroperoxide is typically used in an excess of 1 to 10 mol equivalents, for example 1.5 to 3 mol equivalents, based on the molar amount of the sterically hindered nitroxyl radical.

The reaction can be carried out in several ways. For instance the sterically hindered nitroxyl radical is dissolved in the aldehyde. If necessary an inert cosolvent is added. To this solution an aqueous solution of the hydroperoxide is added and after a short time of stirring the metal catalyst is added either dissolved in water or in an appropriate solvent or directly, for example, in the form of a powder. The mixture is stirred and reacted for an appropriate time. In another embodiment of the process it is possible to dissolve the aldehyde in an appropriate solvent and to add the hydroperoxide subsequently. After a certain time the hindered nitroxide radical is added, either dissolved in an appropriate solvent or neat, followed by the catalyst. It is also possible to dissolve the hindered nitroxyl radical in an appropriate solvent, adding the catalyst and then adding the aldehyde and the hydroperoxide over the course of time—either simultaneously or one after another.

Preferably, the oxidant is added over the course of time to a solution of the hindered nitroxyl radical and the aldehyde and the metal catalyst in an appropriate solvent or the oxidant and the aldehyde are added over the course of time to a solution of the hindered nitroxyl radical and the metal catalyst.

It is possible to employ at the beginning the whole amount of aldehyde or only a part of it. The remaining amount can then be dosed to the reaction mixture over the desired time. The hydroperoxide and the metal catalyst can as well be completely added initially to the reaction mixture or added in portions over a certain time.

When starting from the N—H precursor, it is also possible to oxidize it to the corresponding nitroxyl radical and then to continue the reaction in one pot to the desired nitroxyl ether.

A specific embodiment of the invention is the process for the preparation of a sterically hindered nitroxyl ether of formula (I) or (II)

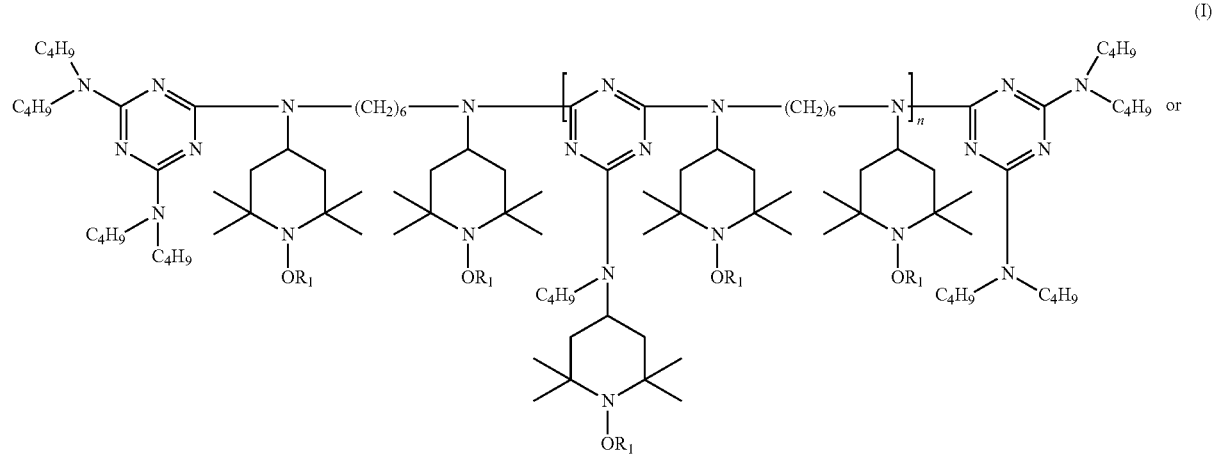
(I)
or
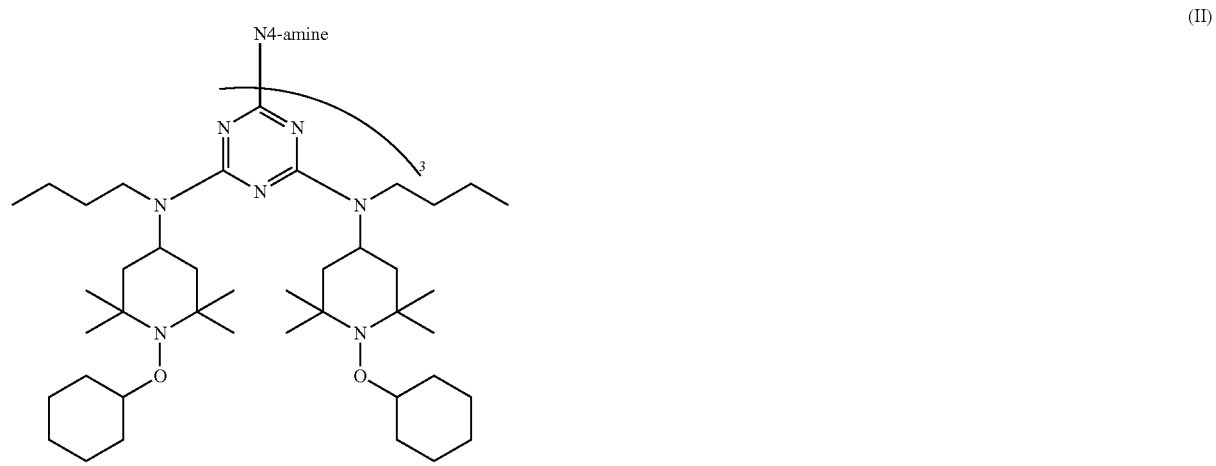
(II)
wherein N4-amine is
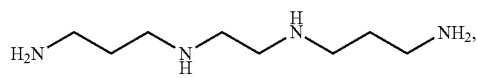 [SMILES: NCCCNCCNCCCN]
n is a number from 1 to 10 and $R_1$ is propyl;
which comprises in the case of the sterically hindered nitroxyl ether of formula (I)
a) reacting a compound of formula (Ia)
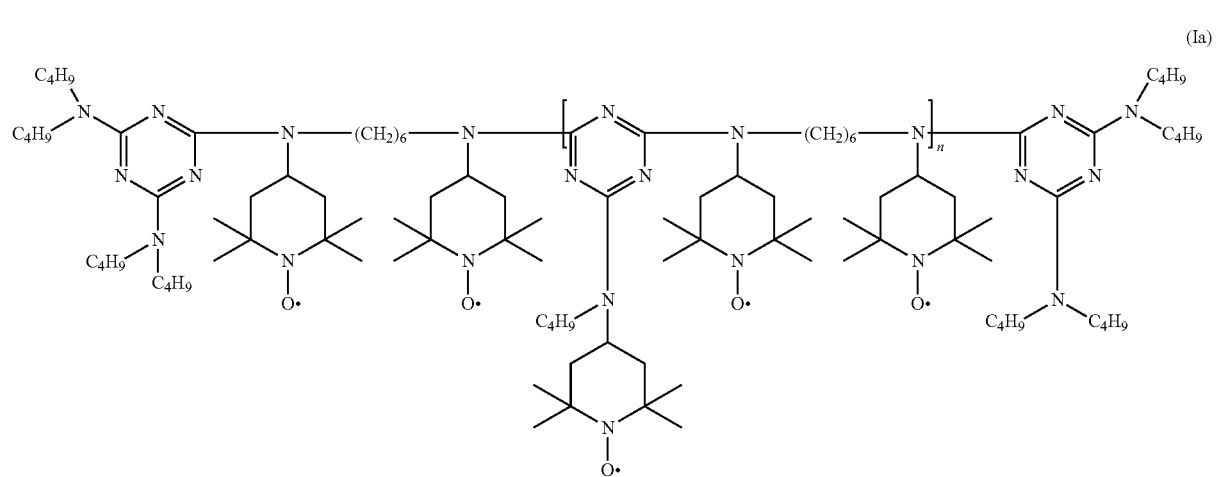
(Ia)

with n-hexylaldehyde, n-pentylaldehyde, n-butyraldehyde, n-propylaldehyde or acetaldehyde and a hydroperoxide in the presence of a metal catalyst; or b1) reacting a compound of formula (Ib)

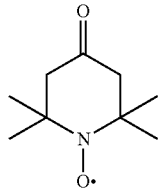

with n-hexylaldehyde, n-pentylaldehyde, n-butyraldehyde, n-propylaldehyde or acetaldehyde or a mixture of said aldehydes with their respective alcohols and a hydroperoxide in the presence of a metal catalyst to yield a compound of formula (Ic)

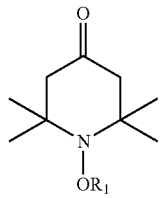

and b2) further reacting the compound of formula (Ic) with butylamine and subsequent hydrogenation to yield the compound of formula (Id)

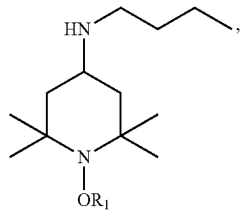
(Id)

which is reacted with cyanuric chloride to the compound of formula (Ie)

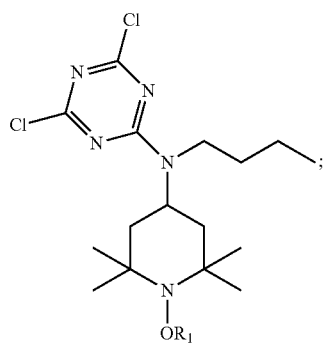

and reacting the compound of formula (Ic) with 1,6-diaminohexane and subsequent hydrogenation to yield the compound of formula (If)

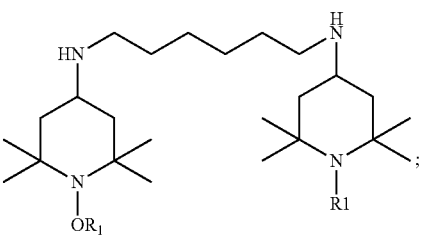

and b3) reacting the compound of formula (Ie) and (If) to yield the compound of formula (I);

which comprises in the case of the sterically hindered nitroxyl ether of formula (II)

a) reacting a compound of formula (IIa) or (IIb)

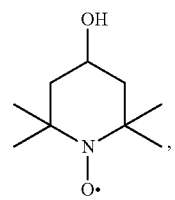
(IIa)

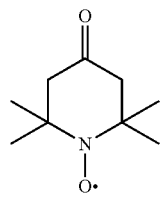
(IIb)

with a compound of formula (100) or (200)

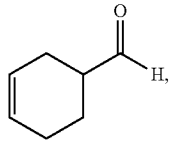
(100)

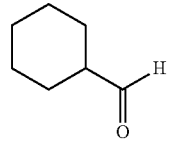
(200)

and a hydroperoxide in the presence of a metal catalyst to yield a compound of formula (IIc), (IId), (IIe) or (IIf)

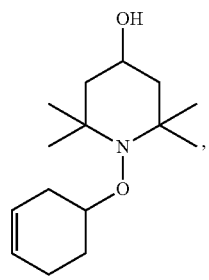
(IIc)

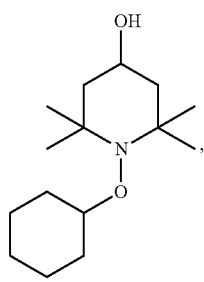

(IId)

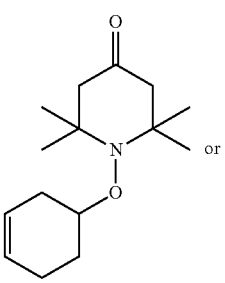

(IIe)

or

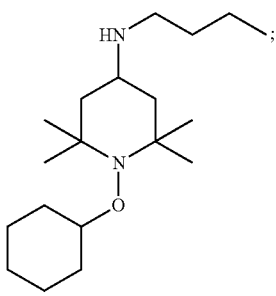

(IIf)

b1) further reacting
the compounds (IIe) or (IIf) directly with n-butylamine followed by hydrogenation and the compounds of formula (IIc) or (IId) after protecting the alcohol group with, a protective group with n-butylamine followed by hydrogenation to yield a compound of formula (IIg)

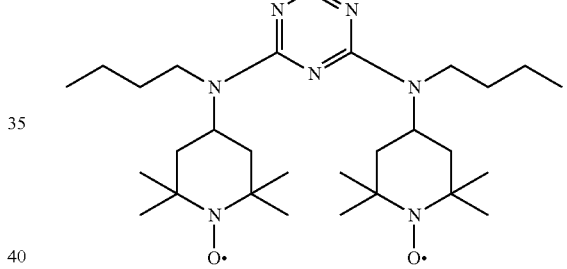

(IIg)

b2) reacting the compound of formula (IIg) with cyanuric chloride to yield the compound of formula (IIh)

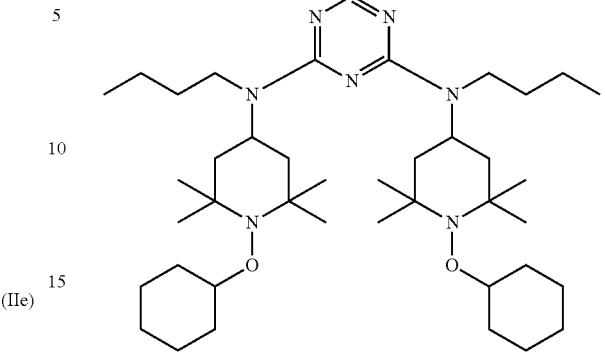

(IIh)

which is reacted with $H_2N$—$\underset{H}{N}$—$\underset{H}{N}$—$NH_2$

N4-amine to yield the compound of formula (II); or alternatively
b3) reacting the compound of formula (IIi)

(IIi)

with compound 100 or 200 and a hydroperoxide in the presence of a metal catalyst followed by subsequent hydrogenation where appropriate to yield compound (IIh), which is further reacted with N4-amine to yield the compound of formula (II).

The further reactions of the intermediate nitroxylethers are known reactions and are standard procedures of organic chemistry.

When $R_1$ in formula (I) is propyl the resulting compound of formula (I) is Tinuvin NOR 371® a light stabilizer of Ciba Specialty Chemicals.

The compound of formula (II) is Flamestab 116® a flame retardant of Ciba Specialty Chemicals.

The sterically hindered nitroxyl radical starting materials are known in the art; they may be prepared by oxidation of the corresponding N—H sterically hindered amine with a suitable oxygen donor, e.g. by the reaction of the corresponding N—H sterically hindered amine with hydrogen peroxide and sodium tungstate as described by E. G. Rozantsev et al., in Synthesis, 1971, 192; or with tert-butyl hydroperoxide and molybdenum (VI) as taught in U.S. Pat. No. 4,691,015, or obtained in analogous manner.

The precursor compounds of the sterically hindered nitroxyl radicals (sterically hindered NH compounds) are essentially known and commercially available. All of them can be prepared by known processes. Their preparation is disclosed, for example, in:

U.S. Pat. No. 5,679,733, U.S. Pat. No. 3,640,928, U.S. Pat. No. 4,198,334, U.S. Pat. No. 5,204,473, U.S. Pat. No. 4,619,958, U.S. Pat. No. 4,110,306, U.S. Pat. No. 4,110,334, U.S. Pat. No. 4,689,416, U.S. Pat. No. 4,408,051, SU-A-768,175 (Derwent 88-138,751/20), U.S. Pat. No. 5,049,604, U.S. Pat. No. 4,769,457, U.S. Pat. No. 4,356,307, U.S. Pat. No. 4,619,956, U.S. Pat. No. 5,182,390, GB-A-2,269,819, U.S. Pat. No. 4,292,240, U.S. Pat. No. 5,026,849, U.S. Pat. No. 5,071,981, U.S. Pat. No. 4,547,538, U.S. Pat. No. 4,976,889, U.S. Pat. No. 4,086,204, U.S. Pat. No. 6,046,304, U.S. Pat. No. 4,331,586, U.S. Pat. No. 4,108,829, U.S. Pat. No. 5,051,458, WO-A-94/12,544 (Derwent 94-177,274/22), DD-A-262,439 (Derwent 89-122,983/17), U.S. Pat. No. 4,857,595, U.S. Pat. No. 4,529,760, U.S. Pat. No. 4,477,615, CAS 136,504-96-6, U.S. Pat. No. 4,233,412, U.S. Pat. No. 4,340,534, WO-A-98/51,690 and EP-A-1,803, in particular U.S. Pat. No. 4,442,250 or U.S. Pat. No. 6,046,304.

The oxidation may be carried out in analogy to the oxidation of 4-hydroxy-2,2,6,6-tetramethylpiperidine described in U.S. Pat. No. 5,654,434 with hydrogen peroxide. Another also suitable oxidation process is described in WO 00/40550 using peracetic acid.

An exhaustive description of the nitroxide (nitroxyl radical) chemistry can be found, for example, in L. B. Volodarsky, V. A. Reznikov, V. I. Ovcharenko.: "Synthetic Chemistry of Stable Nitroxides", CRC Press, 1994.

The following examples illustrate the invention.

PREPARATION EXAMPLES

Preparation of a Compound of Formula (I)

The compound of formula (I) is prepared according to the following reaction scheme starting from 1-oxyl 2,2,6,6-tetramethylpiperidine-4-oxo

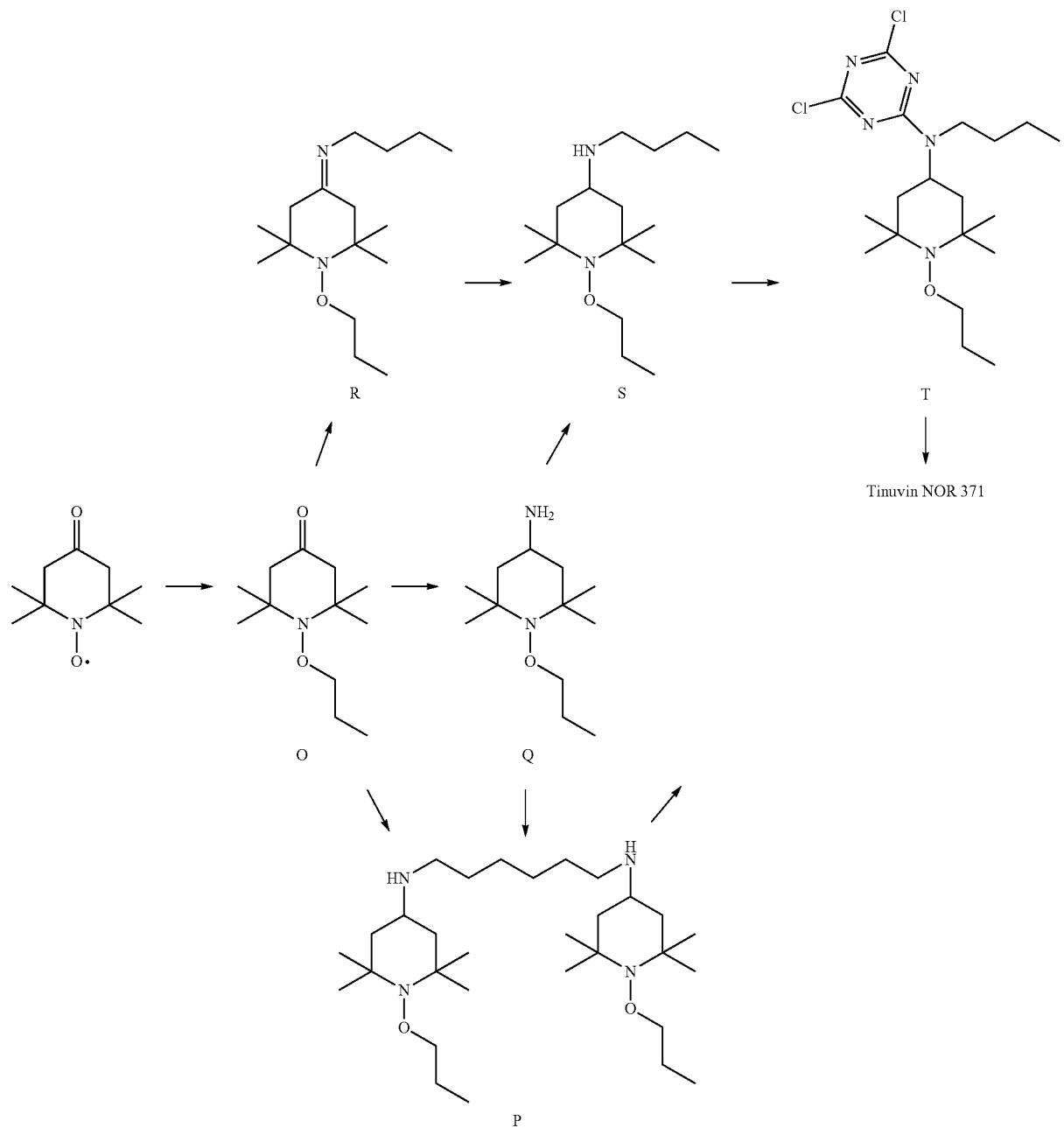

or starting from a compound of formula

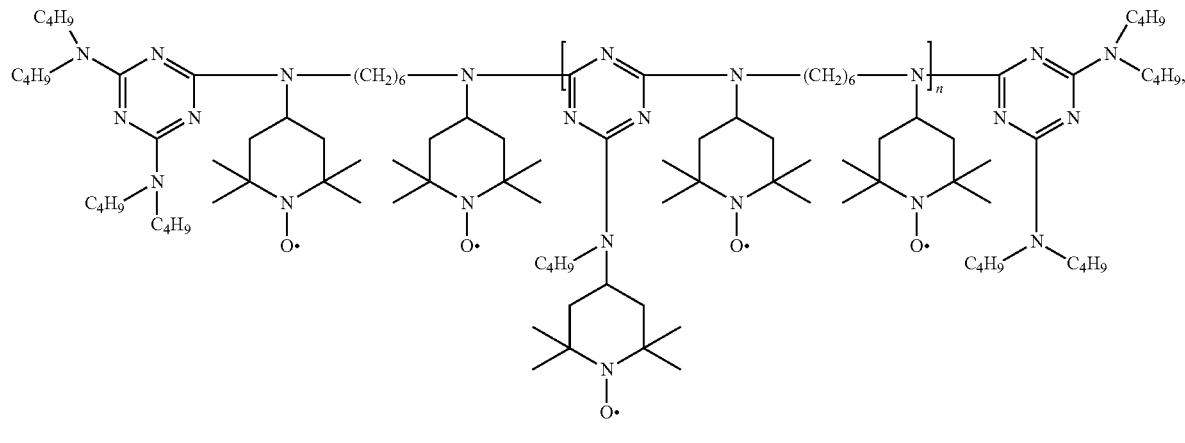

which is the oxidation product of Chimassorb 2020®. Chimassorb 2020 is described in EP 782 994, n is a mixture of numbers between 1 and 10, $M_n$ (by GPC) is approximately 3000 and $M_w/M_n$ is typically 1.2.

In a 1 L jacket reactor, 100 g of Chimassorb 2020 (commercial product of Ciba Specialty Chemicals Inc.) are added to 400 g of toluene. When the product is dissolved, 150 g of anhydrous $Na_2CO_3$ are added. The temperature of the mixture is set to 25° C., and 230 g of 35% peracetic acid solution are added within 5 h, keeping the temperature between 20° C. and 30° C. After the addition is finished, the mixture is stirred for 1.5 h at 25° C. and then heated up to 35° C., and 500 g of water is added. The mixture is heated to 70° C. and stirred at this temperature for 55 min. The mixture is split in two phases and the aqueous phase is separated. Water is removed from the organic phase by azeotropic distillation, to give 490 g of a red solution.

Preparation of the Compound of the Formula mins. The lower turquoise aqueous phase is separated and the organic phase is subsequently washed with aqueous sodium carbonate solution. The mixture is stirred for 15 mins and, after phase splitting, water is removed azeotropically from the organic phase. The solvent is removed by distillation under vacuum to give 116 g of pale yellow foam.

Alternative Synthesis of Tinuvin NOR 371®

Example A 100 g Chimassorb 2020® (commercial product of Ciba Specialty Chemicals Inc.) in t-butanol is reacted with 120 g 50% hydrogen peroxide in the presence of 3 g sodium carbonate decahydrate to afford the Chimassorb 2020-nitroxyl after approximately 7-9 hrs. of reaction at 75° C. The batch is treated with sodium sulfite solution to destroy unreacted per-

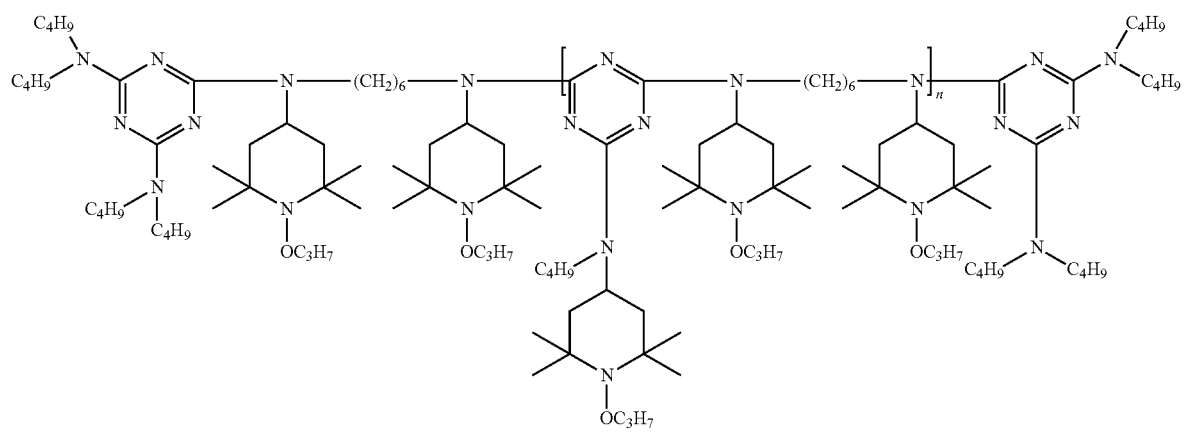

(Tinuvin NOR 371 (RTM), CAS 565450-39-7)

The above resulting solution is cooled to 15° C. and 126 g of 83% acetic acid aqueous solution, 80 g of 30% $H_2O_2$ aqueous solution and 67 g of butanal are added. 2.4 g of CuCl are added at 15° C. The resulting mixture is stirred at 15° C. for 10 h and after for 2 h at 38° C. The stirring is stopped and the two phases are split. 15% aqueous EDTA solution is added and the resulting mixture is stirred at 30-35° C. for 15 oxides and then the aqueous layer is split off. The batch pH is brought to 7 with a trace of glacial acetic acid. Additional 140 g t-butanol is added, followed by 100 g butyraldehyde and 0.2 g Cu(I)Cl. Hydrogen peroxide (120 g) is dosed in while maintaining the reaction temperature at 35° C. The batch is on hold at 35° C. until the reaction is complete. A combination of sodium sulfite and sodium hydroxide solution is added. t-Butanol/water is stripped off under partial vacuum (15-20 mm Hg.) and the t-butanol is replaced by hexane. After 30 min. of stirring at 60° C., the aqueous layer is split. The batch pH is adjusted to 7 with a small quantity of acid. An EDTA wash is performed and the product is isolated with hot water stripping and dried in an oven at 80° C. to constant weight. Yield: 117 g; yellow powder.

Alternative Synthesis of Tinuvin NOR 371®

Example B

In a stainless steel autoclave, to 50 g Chimassorb 2020® (commercial product of Ciba Specialty Chemicals Inc.) in t-butanol are added 70 g 50% hydrogen peroxide. The autoclave is pressurized with 2 bar carbon dioxide and slowly heated to 58° C. The reaction mixture is stirred for 12 h to afford Chimassorb 2020-nitroxyl. The reaction mixture is added to 100 g t-butanol, and 55 g butyraldehyde and 0.2 g Cu(I)Cl are added. Hydrogen peroxide (65 g) is dosed in while maintaining the reaction temperature at 35° C. The batch is on hold at 35° C. until the reaction is complete. 250 ml 10% aqueous sodium carbonate solution are slowly and the mixture is stirred at 70° C. for 2.5 h. The aqueous phase is split off. t-Butanol/water is stripped off under partial vacuum (15-20 mm Hg) and the t-butanol is replaced by toluene. The batch pH is adjusted to 7 with a small quantity of acid. An EDTA wash is performed and the product is isolated with hot water stripping and dried in an oven at 80° C. to constant weight. Yield: 51 g; tan foam.

Alternative Method for the Preparation of TINUVIN 371 from Chimassorb 2020-nitroxyl Example C Chimassorb 2020-nitroxyl (5 g) is dissolved in butanol (20 ml) at 60°. A solution of sodium chloride (1.36 g) in water (25 ml) is added, followed by butanal (9 ml). The emulsion is stirred at 60°, and 30% hydrogen peroxide (7 ml) is added dropwise during 30 min. The mixture is heated slowly to 90° and stirred at 90° for 4-8 h.

Workup: The aqueous phase is separated and discarded. The organic phase is extracted with water (50 ml), then added dropwise to methanol (300 ml). Water (50 ml) is added with stirring, and the pH-value is adjusted to 8-9 by adding aqueous sodium carbonate solution. The precipitate is filtered off and washed several times with water, then dried in vacuo overnight at 60°. Yield: 4.64 g (77%), off-white powder.

Alternative Method for the Preparation of TINUVIN 371

Example D

Chimassorb 2020 (commercial product of Ciba Specialty Chemicals Inc.) (10 g) is dissolved in t-butanol (13.2 ml) at 78°. After cooling to 45° a solution of 34 mg sodium tungstate dihydrate in water (2 ml) is added. 50% Hydrogen peroxide in water (16.8 ml) is added dropwise at 45°. The mixture is stirred at 45° for 18 h.

Sodium chloride (2.72 g) is dissolved in water (13.2 ml) and added to the reaction mixture, followed by butanal (18.2 ml). 30% Hydrogen peroxide in water (14.3 ml) is added dropwise at 53°. The mixture is stirred at 78-82° for 5 h.

Workup: The aqueous phase is separated and discarded. The remaining organic phase is added dropwise to methanol (200 ml). The pH is adjusted to 8-9 with aqueous sodium carbonate solution. The mixture is stirred for 1 h at 25°, and the precipitate is filtered off, washed several times with water, and dried in vacuo at 60° overnight. Yield 11.43 g (95%), off-white powder.

Method for the Preparation of a Compound of the Formula

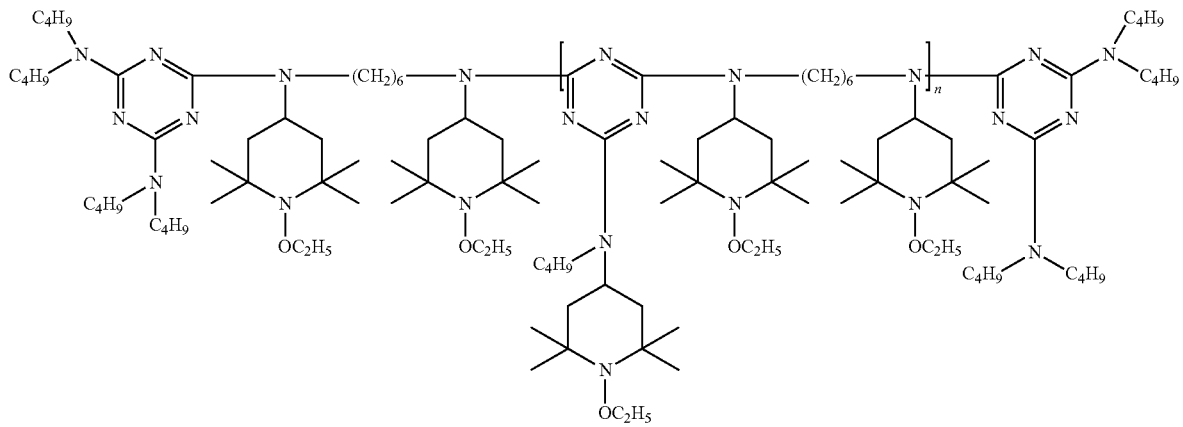

To a solution of 48.3 g Chimassorb 2020-nitroxyl in 150 ml toluene are added 10 g of acetic acid, 8 g of 30% aqueous $H_2O_2$ solution and 6.8 g of propionaldehyde. 0.2 g CuCl are added at RT. The resulting mixture is stirred for 10 h at 35° C.; another 4 g of 30% $H_2O_2$ are added and stirring is continued for 4 h at 48° C. The stirring is stopped and the two phases are split. 15% aqueous EDTA solution is added and the resulting mixture is stirred at 30-35° C. for 15 mins. The lower turquoise aqueous phase is separated and the organic phase is subsequently washed with aqueous sodium carbonate solution. The mixture is stirred for 15 mins and, after phase splitting, water is removed azeotropically from the organic phase. The solvent is removed by distillation under vacuum to give 9.8 g of pale yellow foam. The presence of ethoxy groups was proven by NMR.

Method for the Preparation of a Compound of the Formula

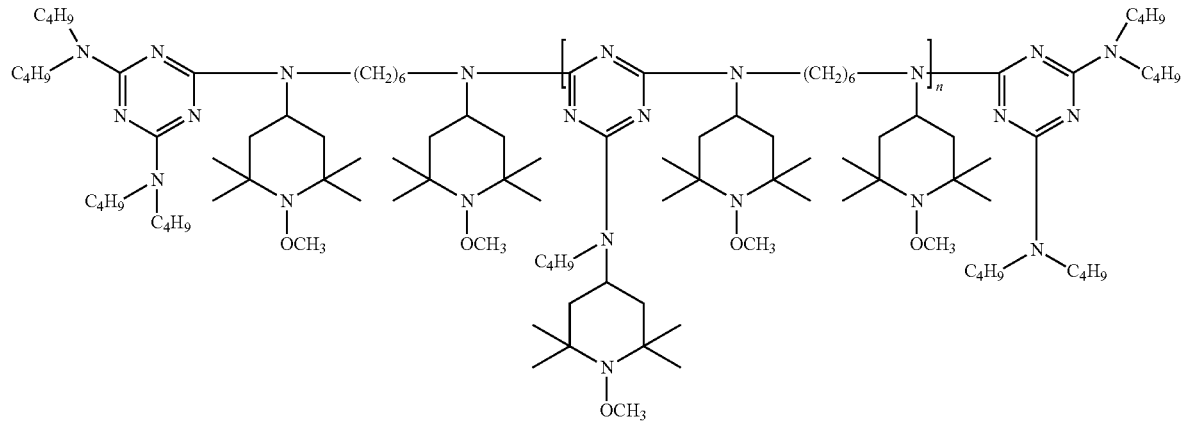

Chimassorb 2020-nitroxyl (5 g) is dissolved in butanol (20 ml) at 60°. A solution of sodium chloride (1.36 g) in water (25 ml) is added, followed by acetaldehyde (10 ml). The emulsion is stirred at 60°, and 30% hydrogen peroxide (7 ml) is added dropwise during 30 min. The mixture is heated slowly to 90° and stirred at 90° for 7 h.

Workup: The aqueous phase is separated and discarded. The organic phase is extracted with water (50 ml), then added dropwise to methanol (300 ml). Water (50 ml) is added with stirring, and the pH-value is adjusted to 8-9 by adding aqueous sodium carbonate solution. The precipitate is filtered off and washed several times with water, then dried in vacuo overnight at 60°. Yield: 4.35 g (69%), off-white powder.

Starting from
1-oxy-2,2,6,6-tetramethyl-piperidin-4-one

1-Propoxy-2,2,6,6-tetramethyl-piperidin-4-one, Compound O (the Letters Refer to the Scheme Above)

76.5 g (446 mmol) triacetoneamine-N-oxyl are dissolved in 350 ml ethanol and 20 ml water. 43 g butanal, 1.5 g acetic acid and 0.65 g CuCl are added at room temperature. 57 ml of a 30% aqueous hydrogen peroxide solution are dosed in over a period of 2 h, keeping the reaction temperature at 25-30° C. After 6 h another 15 ml of hydrogen peroxide solution are added. After 24 h, the green solution is diluted with 300 ml tert-butylmethyl ether and the two phases are separated. The organic phase is washed with 10% ascorbic acid solution, water, diluted sodium carbonate sol., diluted sodium chloride sol., and saturated sodium chloride sol. The organic phase is dried over sodium sulfate and finally evaporated to complete dryness under vacuum to afford 91 g of a blue oil. The product is purified by means of distillation (b.p. 75-80° C., 0.1 mbar) to afford 78.1 g (82%) product.

NMR-data: $^1$H-NMR (CDCl$_3$), δ (ppm): 0.95 (t, 3H), 1.14 (s, 6H), 1.28 (s, 6H), 1.55 (m, 2H), 2.33 (d, 2H), 2.54 (d, 2H), 3.81 (t, 2H).

$^{13}$C-NMR (CDCl$_3$), δ (ppm): 10.9, 21.8, 22.5, 32.5, 53.3, 62.9, 78.4.

Butyl-[1-(propoxy)-2,2,6,6-tetramethyl-piperidin-4-ylidene]-amine, Compound R 18.7 g (81.5 mmol) compound O are dissolved in 100 ml methanol and 7.0 g n-butylamine and 10 g sodium sulfate are added. The mixture is stirred at RT until 13C-NMR spectroscopy indicates the disappearance of the starting material. Filtration of the reaction mixture and evaporation of the organic solvent give 21.4 g pure product (98%); oil.

NMR data: $^1$H-NMR (CDCl$_3$), δ (ppm): 0.93 (2t, 6H), 1.04 (s, 3H), 1.09 (s, 3H), 1.25 (s, 3H), 1.28 (s, 3H), 1.35 (m, 2H), 1.49-1.61 (m, 4H), 2.0 (d, 1H), 2.20 (m, 1H), 2.41 (d, 1H), 2.58 (m, 1H), 3.37 (m, 2H), 3.75 (m, 2H).

$^{13}$C-NMR (CDCl$_3$), δ (ppm): 10.9, 14.0, 20.7, 21.9, 32.4, 33.1, 40.9, 50.5, 51.1, 61.8, 62.2, 78.4, 167.8.

Butyl-(1-propoxy-2,2,6,6-tetramethyl-piperidin-4-yl)-amine, Compound S

In a stainless steel autoclave 0.5 g 10% palladium on charcoal are added to a solution of 21.4 g (79.7 mmol) compound R in 100 ml methanol. The autoclave is pressurized with 5 bar of hydrogen and stirred at 60-75° C. for 20 h. The reaction mixture is filtered over celite and the methanol removed in vacuo to give 21.1 g (96%) of a yellowish solid.

NMR data: $^1$H-NMR (CDCl$_3$), δ (ppm): 0.93 (m, 6H), 1.17 (s, 6H), 1.19 (s, 6H), 1.2-1.31 (m, 2H), 1.32-1.37 (m, 2H), 1.41-1.47 (m, 2H), 1.51-1.56 (m, 2H), 1.71-1.74 (m, 2H), 2.59 (t, 2H), 2.73-2.78 (m, 1H), 3.69 (t, 2H).

$^{13}$C-NMR (CDCl$_3$), δ (ppm): 11.0, 14.0, 20.6, 21.0, 21.8, 32.8, 33.3, 46.8, 48.2, 59.8, 78.4.

In analogy, 1-propoxy-2,2,6,6-tetramethyl-piperidin-4-yl-amine, compound Q, can be prepared using a 7M solution of ammonia in methanol, followed by hydrogenation NMR data: $^{13}$C-NMR (CDCl$_3$), δ (ppm): 10.9, 20.9, 21.9, 33.1, 33.2, 42.1, 49.8, 59.7, 59.8, 78.3.

This compound can be transformed into butyl-(1-propoxy-2,2,6,6-tetramethyl-piperidin-4-yl)-amine, compound S, or N,N'-Bis-(2,2,6,6-tetramethyl-1-propoxy-piperidin-4-yl)-hexane-1,6-diamine, compound P, by known methods (e.g. reductive amination or alkylation employing butyl bromide/chloride).

N,N'-Bis-(2,2,6,6-tetramethyl-1-propoxy-piperidin-4-yl)-hexane-1,6-diamine, Compound P A mixture of 32.5 g (0.15 mol) compound O, 9.3 g (0.55 eq.) 1,6-diaminohexane, 220 ml methanol and 0.75 g 10% Pd/C is hydrogenated over night at 70° C. and 25 bar. The reaction mixture is filtered and volatiles are evaporated to yield 38.8 g (100%) of a slightly brown, viscous oil.

NMR data: $^1$H-NMR (CDCl$_3$), δ (ppm): 0.95 (t, 6H), 1.15 (s, 12H), 1.18 (s, 12H), 1.20-1.26 (m, 4H), 1.34-1.36 (br m, 4H), 1.46-1.49 (m, 4H), 1.51-1.58 (m, 4H), 1.72-1.75 (m, 4H), 2.60 (t, 4H), 2.75-2.80 (m, 2H), 3.71 (t, 4H).

$^{13}$C-NMR (CDCl$_3$), δ (ppm): 11.0, 21.0, 22.0, 27.4, 30.6, 33.2, 46.6, 47.0, 48.1, 59.7, 78.5.

Butyl-(4,6-dichloro-1,3,5-triazin-2-yl)-(2,2,6,6-tetramethyl-1-propoxy-piperidin-4-yl)-amine, Compound S To a suspension of 24 g (0.13 mol) cyanuric chloride in 125 ml xylene are slowly added 35.2 g (0.13 mol) compound R at 5-10° C. The mixture is allowed to warm up to 40° C. followed by the addition of 29 g (0.145 mol) NaOH (aqueous 20%). After stirring for 2.5 h at 40° C., a sample is taken and analyzed. GLC indicates >98% conversion. The structure is confirmed by NMR.

Preparation of Tinuvin NOR 371® Using Compounds S and P

Continuation of the preceding example: The aqueous phase is split off and the organic phase heated to 70° C. followed by the slow addition of 33.2 g (0.065 mol) compound P and 33 g water. After addition of 20 g (0.15 mol) 30% aqueous sodium hydroxide solution, the mixture is stirred at 80° C. for 2 h. The structure is confirmed by NMR. The hot aqueous phase is split off. The organic phase is cooled down to 25° C. and transferred into an autoclave. After addition of 66.4 g (0.13 mol) compound P and 28.6 g (0.143 mol) NaOH (aqueous 20%) the autoclave is sealed and heated to 175° C. where it is left for 4 hours. After cooling down to 25° C. the autoclave is unloaded and the aqueous phase split off (at 80° C.). The structure is confirmed by NMR. Mn/Mw (GPC) 1700/3300-1900/3800. Amount of residual compound P approximately 6% (area %).

Further reaction with 2-chloro-4,6-bis(dibutylamino)-s-triazine yields Tinuvin NOR 371®.

Preparation of the Compound of Formula (II)

The compound of formula (II) is prepared according to the following reaction scheme starting from triacetonamine and from the corresponding 4-hydroxy-2,2',6,6'-tetramethylpiperidine-1-oxyl. An alternative is to use compound TH-7 as starting material as outlined below.

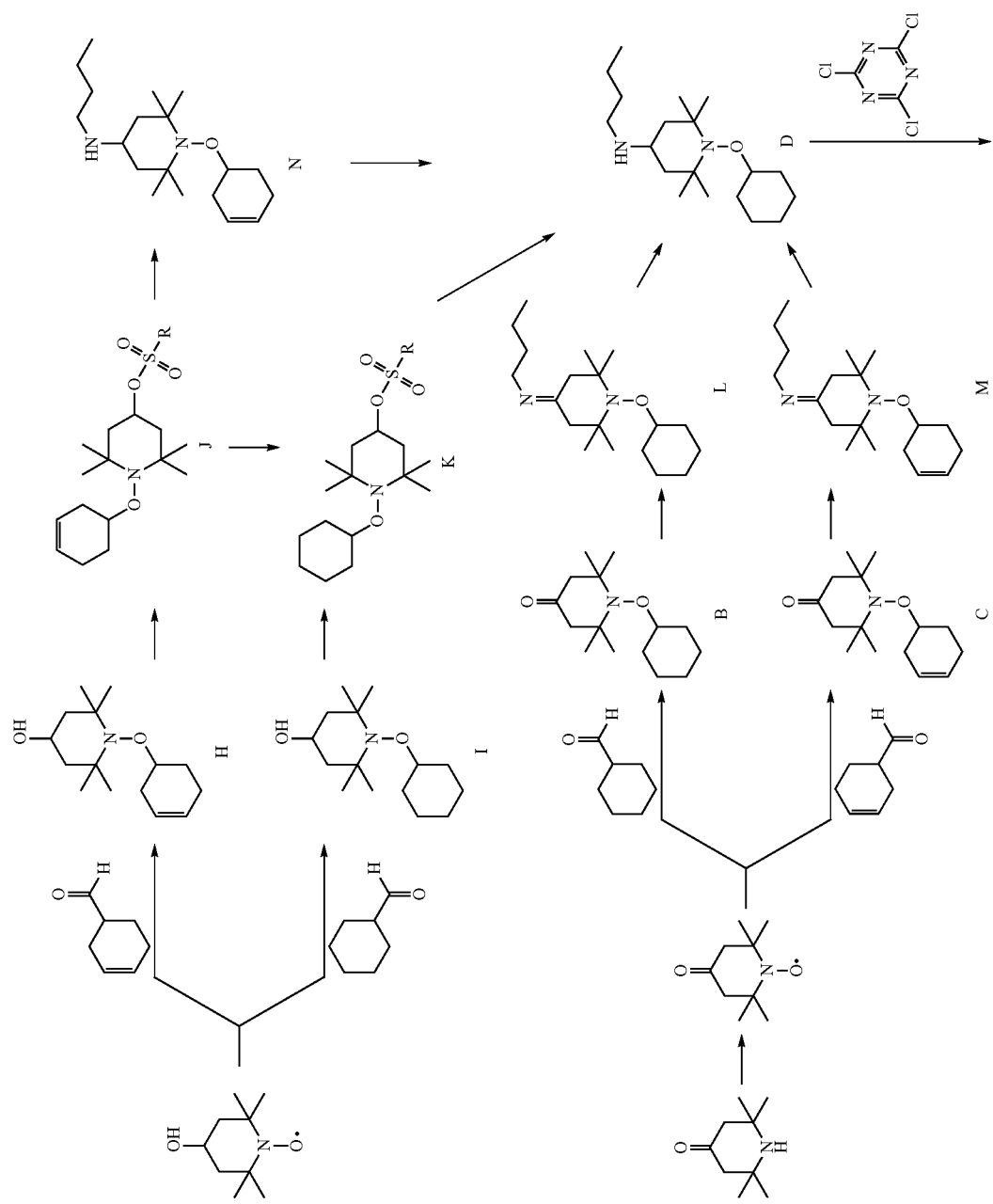

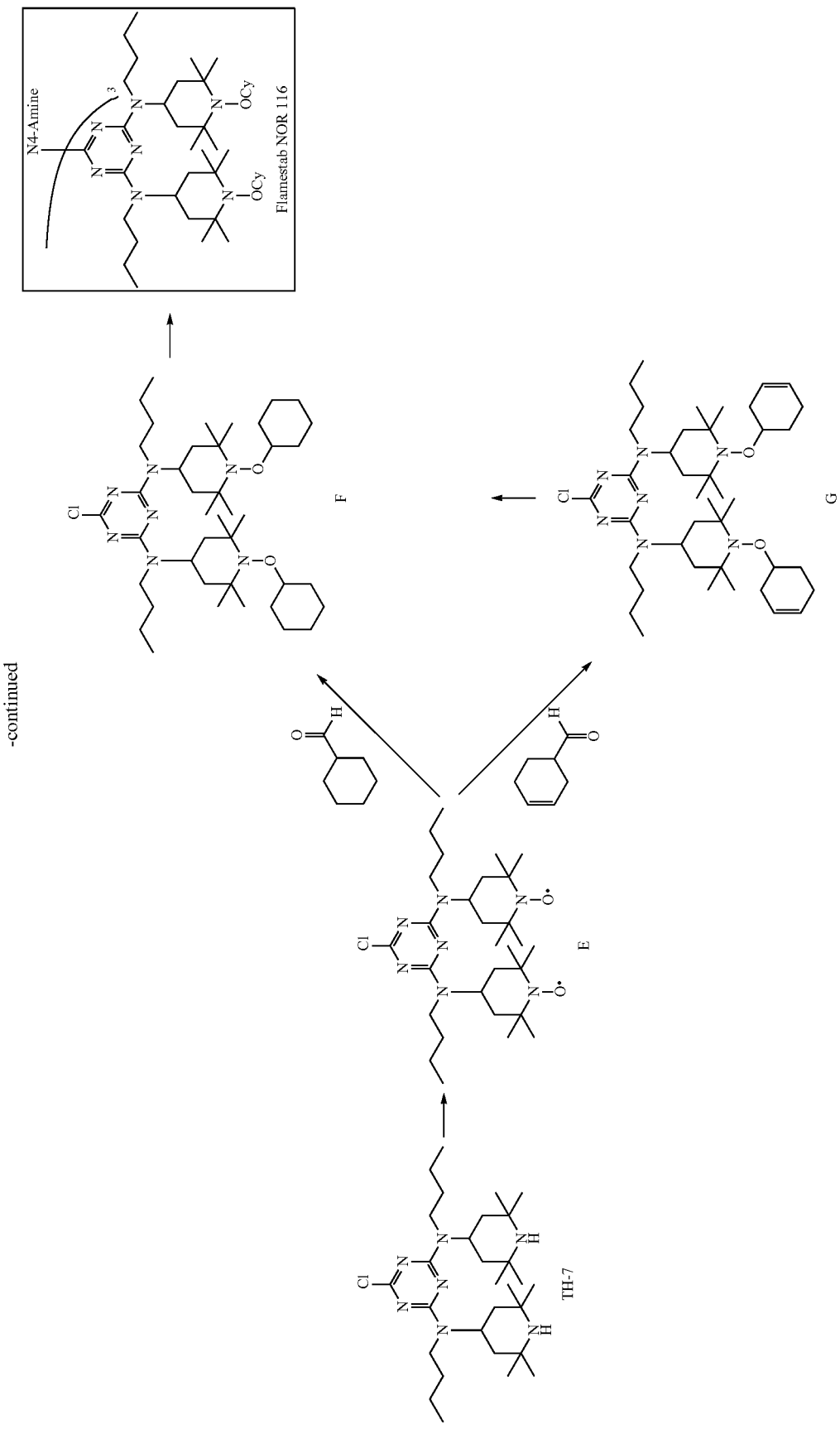

Triacetoneamine-N-oxyl

To a stirred mixture of 50.0 g (0.322 mol) triacetoneamine, 3.94 g (0.01 mol) sodium tungstate dihydrate and 250 ml water are added at 5° C. and within 1 hour 71.4 g (0.63 mol) aqueous 30% hydrogenperoxide. The orange mixture is warmed to 25° C. and stirring is continued for 21 hours. Potassium carbonate is then added until phase separation occurs and the triacetoneamine-N-oxyl extracted three times with a total of 150 ml tert-butylmethyl ether. The organic solvent is completely removed in vacuo to yield 51.5 g (94%) product.

1-Cyclohex-3-enyloxy-2,2,6,6-tetramethyl-piperidin-4-one, Compound C (the Letters Refer to the Scheme Above)

6.8 g (39.9 mmol) triacetoneamine-N-oxyl are dissolved in a 2:1 mixture of ethanol and water. 4.5 g of 1,2,3,6-tetrahydrobenzaldehyde are added followed by 5.7 g 30% aqueous hydrogen peroxide and 54 mg copper(II)chloride. The mixture is stirred at 25-35° C. for 24 h. After 12 h another 3.8 g of H2O2 are added. The green reaction mixture is diluted with 80 ml tert-butylmethyl ether and subsequently washed with 20 ml 0.1N NaOH, twice with water and sat. sodium chloride sol. The organic phase is dried over sodium sulfate and finally evaporated to complete dryness under vacuum to afford 7.22 g product (72%); solid; GC purity >95%.

NMR data: $^1$H-NMR (CDCl$_3$), δ (ppm): 1.21 (s, 3H), 1.30 (s, 3H), 1.55 (m, 1H), 2.03-2.31 (m, 6H), 2.41 (m, 2H), 2.60 (m, 2H), 4.03 (m, 1H), 5.60 (m, 2H).

$^{13}$C-NMR (CDCl$_3$), δ (ppm): 23.0 (2C), 25.0, 28.6, 31.5, 34.1 (2C), 53.5, 79.1, 124.5, 126.8, 208.6.

1-Cyclohexyloxy-2,2,6,6-tetramethyl-piperidin-4-one, compound B, can be prepared in analogy using Cyclohexanecarboxaldehyde Yield 64%; solid
NMR data: $^{13}$C-NMR (CDCl$_3$), δ (ppm): 22.9, 23.3, 25.0, 25.8, 32.4, 32.7, 34.0, 53.4, 62.9, 82.5, 208.8.

Butyl-[1-(cyclohex-3-enyloxy)-2,2,6,6-tetramethyl-piperidin-4-ylidene]-amine, Compound M 2.5 g (9.9 mmol) compound C are dissolved in 15 ml methanol and 0.78 g n-butylamine and 2 g sodium sulfate are added. The mixture is stirred at Rt until 13C-NMR spectroscopy indicates the disappearance of the starting material. Filtration of the reaction mixture and evaporation of the organic solvent give 3.0 g pure product (99%); oil.

NMR data: $^1$H-NMR (CDCl$_3$), δ (ppm): 0.94 (t, 3H), 1.03-1.71 (m, 16H), 2.01-2.29 (m, 6H), 2.41 (m, 2H), 2.60 (m, 2H), 3.30 (m, 2H), 4.00 (m, 1H), 5.59 (m, 2H).

$^{13}$C-NMR (CDCl$_3$), δ (ppm): 14.0, 20.7, 20.8, 21.3, 25.0, 26.2, 27.1, 28.7, 31.7, 41.3, 50.7, 51.8, 61.8, 62.3, 78.8, 125.0, 126.8, 167.4.

In analogy, butyl-(1-cyclohexyloxy-2,2,6,6-tetramethyl-piperidin-4-ylidene)-amine, compound L, can be prepared starting from compound B.

$^{13}$C-NMR (CDCl$_3$), δ (ppm): 14.0, 20.7, 23.8, 25.8, 29.7, 33.1, 41.4, 50.5, 51.4, 61.8, 62.2, 82.0, 168.3.

Butyl-(1-cyclohexyloxy-2,2,6,6-tetramethyl-piperidin-4-yl)-amine, Compound D

In a 400 ml stainless steel autoclave 2.0 g 10% palladium on charcoal are added to a solution of 30 g (98 mmol) compound M in 200 ml methanol. The autoclave is pressurized with 5 bar of hydrogen and stirred at 60° C. for 2.5 h. The reaction mixture is filtered over celite and the methanol removed in vacuo. The obtained oily material is subjected to column chromatography (hexane/acetone 4:1; 0.5% triethylamine) to give 28.1 g (94%) pure product; white solid.

NMR data: $^1$H-NMR (CDCl$_3$), δ (ppm): 0.91 (t, 3H), 1.10-1.28 (m, 20H), 1.34 (m, 2H), 1.47 (m, 2H), 1.53 (m, 1H), 1.73 (m, 4H), 2.06 (s, 1H), 2.61 (m, 2H), 2.75 (m, 1H), 3.59 (m, 1H).

$^{13}$C-NMR (CDCl$_3$), δ (ppm): 14.0, 20.5, 20.8, 21.3, 25.0, 26.1, 32.8, 33.7, 35.0, 46.7, 47.2, 48.2, 59.8, 81.9.

The same product can be prepared in analogy starting from butyl-(1-cyclohexyloxy-2,2,6,6-tetramethyl-piperidin-4-ylidene)-amine, compound L. Yield: 98%; white solid.

2,4-bis-[1-cyclohexyloxy-2,2,6,6-tetramethyl-piperidin-4-yl)butylamino]-6-chloro-s-triazine, Compound F 5.0 g (16.1 mmol) of butyl-(1-cyclohexyloxy-2,2,6,6-tetramethyl-piperidin-4-yl)-amine are added to a mixture of 1.49 g cyanuric chloride and 35 ml xylene at 40° C. Sodium hydroxide is added and the mixture is stirred at 70° C. until the reaction is complete. The mixture is cooled and water is added. The organic phase is washed with 1N HCl and water, dried over sodium sulfate, and the organic phase is removed in vacuo. Yield: 5.9 g (quant.); white foam.

NMR data: $^1$H-NMR (CDCl$_3$), δ (ppm): 0.94 (m, 6H), 1.15-1.40 (m, 39H), 1.49-1.61 (m, 10H), 1.62-1.82 (m, 8H), 2.05 (m, 4H), 3.32 (m, 4H), 3.61 (m, 2H), 5.00 (m, 2H).

$^{13}$C-NMR (CDCl$_3$), δ (ppm): 13.9, 14.0, 20.3, 20.5, 20.6, 20.8, 25.1, 25.9, 31.8, 31.9, 32.9, 34.6, 42.3, 42.5, 43.0, 43.5, 46.0, 46.1, 46.3, 60.2, 60.3, 81.9, 82.0, 164.6, 164.8, 168.9.

2,4-bis-[1-oxyl-2,2,6,6-tetramethyl-piperidin-4-yl)butylamino]-6-chloro-s-triazine, Compound E 25 g N,N'-Dibutyl-6-chloro-N,N'-bis-(2,2,6,6-tetramethyl-piperidin-4-yl)-[1,3,5]triazine-2,4-diamine are dissolved in 70 ml toluene. The mixture is cooled to 10° C. and 24.8 g (2.8 eq.) 40% peracetic acid are added over a period of 3 h. The mixture is stirred over night at 30° C. The mixture is diluted with 100 ml toluene and washed with sat. sodium carbonate solution, water and sat. sodium chloride solution. After drying over sodium sulfate, the organic solvent is removed in vacuo to yield a red oily residue which turns into a red solid upon standing.

Yield: 12.6 g (48%).

2,4-bis-[(1-cyclohexyloxy-2,2,6,6-tetramethyl-piperidin-4-yl)butylamino]-6-chloro-s-triazine, Compound F 6.0 g (10.6 mmol) 2,4-bis-[(1-oxyl-2,2,6,6-tetramethyl-piperidin-4-yl)butylamino]-6-chloro-s-triazine are dissolved in 30 ml toluene, 30 ml t-BuOH and 2 ml acetic acid. 2.4 g cyclohexanecarboxaldehyde (2 eq.) and 37 mg CuCl are added. 5.0 g (4 eq.) 30% aqueous H2O2 are added over 1.5 h. The mixture is stirred over night at 40° C. The mixture is diluted with 100 ml TBME and washed with 20% sodium sulfite solution, sat. sodium carbonate solution, water and sat. sodium chloride solution. After drying over sodium sulfate, the organic solvent is removed in vacuo. The residue is subjected to column chromatography (hexane/ethyl acetate 99:1) to afford 3.3 g (42%) product; white foam.

NMR data: $^1$H-NMR (CDCl$_3$), δ (ppm): 0.94 (m, 6H), 1.15-1.40 (m, 39H), 1.49-1.61 (m, 10H), 1.62-1.82 (m, 8H), 2.05 (m, 4H), 3.32 (m, 4H), 3.61 (m, 2H), 5.00 (m, 2H).

$^{13}$C-NMR (CDCl$_3$), δ (ppm): 13.9, 14.0, 20.3, 20.5, 20.6, 20.8, 25.1, 25.9, 31.8, 31.9, 32.9, 34.6, 42.3, 42.5, 43.0, 43.5, 46.0, 46.1, 46.3, 60.2, 60.3, 81.9, 82.0, 164.6, 164.8, 168.9.

In analogy, 2,4-bis-[(1-cyclohex-3-enyloxy-2,2,6,6-tetramethyl-piperidin-4-yl)butylamino]-6-chloro-s-triazine, compound G, can be prepared using 1,2,3,6-tetrahydrobenzaldehyde.

Yield: 30%; white, waxy solid.

NMR data: $^1$H-NMR (CDCl$_3$), δ (ppm): 0.8-1.0 (m, 6H), 1.11-1.34 (m, 32H), 1.42-1.80 (m, 10H), 1.96-2.23 (m, 8H), 2.43 (m, 2H), 3.32 (m, 4H), 3.60 (m, 1H), 3.92 (m, 2H), 4.99 (m, 2H), 5.58 (m, 4H).

$^{13}$C-NMR (CDCl$_3$), δ (ppm): 13.9, 14.0, 14.1, 20.0 (div.), 20.9, 21.0, 25.0, 29.0, 32.0 (div.), 33.1, 33.2, 34.6, 42.0, 42.5, 43.0, 46.0, 46.1, 46.3, 60.0, 65.4, 78.8, 78.9, 125.0, 126.7, 164.1, 164.5, 168.4.

Hydrogenation of 2,4-bis-[(1-cyclohex-3-enyloxy-2,2,6,6-tetramethyl-piperidin-4-yl)butylamino]-6-chloro-s-triazine, compound G, in toluene (10% Pd/C, 5 bar H$_2$, 60° C.) affords 2,4-bis-[(1-cyclohexyloxy-2,2,6,6-tetramethyl-piperidin-4-yl)butylamino]-6-chloro-s-triazine, compound F. Yield: 97%; white foam.

1-Cyclohexyloxy-2,2,6,6-tetramethyl-piperidin-4-ol, Compound I 1.0 g (5.8 mmol) 1-oxyl-2,2,6,6-tetramethyl-piperidin-4-ol (Prostab 5198, commercial product of Ciba Specialty Chemicals Inc.) is dissolved in 5 ethanol/water (1:1) and 2 ml cyclohexane-carboxaldehyde, followed by 5 ml of a 30% aqueous hydrogen peroxide solution are added. At RT, 25 mg CuCl are added. The reaction mixture is stirred over night at room temperature to give a greenish solution. 30 ml tert-butylmethyl ether are added and the two phases are separated. The organic phase is washed with 10% ascorbic acid solution, water, dil. sodium carbonate sol., dil. sodium chloride sol., and saturated sodium chloride sol. It is dried over sodium sulfate and finally evaporated to complete dryness under vacuum. The product is purified by column chromatography (hexane/acetone 13:1) to afford 1.05 g (70%) product; white solid.

NMR: $^1$H-NMR (CDCl$_3$), δ (ppm): 1.13 (s, 3H), 1.20 (s, 3H), 1.1-1.3 (m, 8H), 1.50 (m, 6H), 1.70 (m, 4H), 2.05 (m, 2H), 3.61 (m, 1H), 3.96 (m, 1H).

$^{13}$C-NMR (CDCl$_3$), δ (ppm): 21.2, 25.0, 25.9, 32.8, 34.5, 48.8, 60.0. 63.4, 81.9.

In analogy, 1-Cyclohex-3-enyloxy-2,2,6,6-tetramethyl-piperidin-4-ol, compound H, can be prepared using 1,2,3,6-tetrahydrobenzaldehyde.

Yield: 78%; white solid.

NMR data: $^1$H-NMR (CDCl$_3$), δ (ppm): 1.16 (s, 6H), 1.22 (s, 6H), 1.49 (m, 2H), 1.83 (m, 2H), 2.04-2.28 (m, 4H), 2.41 (d, 1H), 2.58 (m, 1H), 3.98 (m, 2H), 5.91 (m, 2H).

$^{13}$C-NMR (CDCl$_3$), δ (ppm): 21.3, 25.1, 28.8, 32.0, 34.5, 48.2, 60.2, 63.4, 78.8, 125.0, 126.7.

1-Cyclohexyloxy-2,2,6,6-tetramethyl-piperidin-4-yl-toluene-4-sulfonic acid ester, Compound K 3 g (11.8 mmol) compound I are dissolved in 15 ml methylene chloride, and 1.45 g trietylamine and 2.3 g p-toluenesulfonyl chloride are added at 0° C. The mixture is stirred at RT for 4 h and at 40° C., after addition of further 1.2 g of p-toluenesulfonyl chloride, for 24 h. The reaction mixture is diluted with 50 ml methylene chloride, and the organic phase is washed successively with water, 1N HCl, NaHCO$_3$-sol. and brine. After drying over Na$_2$SO$_4$, the mixture is filtered and the solvent is evaporated under reduced pressure. The brown residue is purified by means of column chromatography (hexane/acetone 49:1→9:1) to afford 3.3 g (69%) product; white solid.

$^1$H-NMR (CDCl$_3$), δ (ppm): 1.04 (s, 3H), 1.1-1.25 (m, 14H), 1.51 (m, 1H), 1.60-1.80 (m, 6H), 1.94 (m, 2H), 2.45 (s, 3H), 3.55 (m, 1H), 4.71 (m, 1H), 7.31 (d, 2H), 7.78 (d, 2H).

$^{13}$C-NMR (CDCl$_3$), δ (ppm): 20.9, 21.6, 25.2, 25.9, 33.1, 34.3, 45.4, 60.0, 75.7, 82.0, 127.6, 129.6, 134.2, 144.5.

In analogy, 1-cyclohex-3-enyloxy-2,2,6,6-tetramethyl-piperidin-4-yl-toluene-4-sulfonic acid ester, compound J, can be prepared using 1-cyclohex-3-enyloxy-2,2,6,6-tetramethyl-piperidin-4-ol. Yield: 63%; white solid.

$^1$H-NMR (CDCl$_3$), δ (ppm): 1.05 (s, 3H), 1.13-1.25 (m, 12H), 1.53 (m, 1H), 1.69 (m, 6H), 2.09 (m, 2H), 2.43 (s, 3H), 3.59 (m, 1H), 5.37 (m, 2H), 7.35 (d, 2H), 7.76 (d, 2H).

$^{13}$C-NMR (CDCl$_3$), δ (ppm): 21.3, 23.8, 25.0, 25.9, 32.4, 32.8, 32.9, 32.9, 33.0, 58.2, 60.7, 76.0, 82.3, 119.9, 127.6, 129.2, 134.1, 136.5, 144.9.

Hydrogenation at this stage (MeOH, 5% Pd/C, 5 bar H$_2$, 40° C.) leads to 1-cyclohexyloxy-2,2,6,6-tetramethyl-piperidin-4-yl-toluene-4-sulfonic acid ester, compound K. Yield: 94%; white solid.

Butyl-(1-cyclohexyloxy-2,2,6,6-tetramethyl-piperidin-4-yl)-amine, Compound D 0.5 g (1.22 mmol) 1-cyclohexyloxy-2,2,6,6-tetramethyl-piperidin-4-yl-toluene-4-sulfonic acid ester are dissolved in 3 ml DMSO. 1.1 eq. N-butylamine are added and the mixture is stirred at 70° C. until TLC analysis shows complete disappearance of the starting material. The mixture is diluted with 15 ml water and extracted with methylene chloride. The organic phase is washed with dil. sodium carbonate sol., dil. sodium chloride sol., and saturated sodium chloride sol., and subsequently dried over sodium sulfate. The organic solvent is removed in vacuo and the remaining oily residue is subjected to column chromatography (hexane/ethyl acetate 5:1, 0.1% triethylamine). Two main fractions were isolated.

Yield: 49 mg (13%) compound D.

78 mg (27%) of 1-cyclohexyloxy-2,2,6,6-tetramethyl-1,2,3,6-tetrahydro-pyridine $^1$H-NMR (CDCl$_3$), δ (ppm): 1.1 (m, 3H), 1.21 (m, 2H), 1.23 (s, 12H), 1.55 (m, 1H), 1.74 (m, 2H), 1.85 (m, 1H), 2.09 (m, 2H), 2.22 (m, 1H), 3.62 (m, 1H), 5.39 (m, 2H).

$^{13}$C-NMR (CDCl$_3$), δ (ppm): 21.3, 23.8, 25.0, 25.9, 32.4, 32.8, 32.9, 32.9, 33.0, 58.2, 60.7, 119.9, 136.6.

In analogy, butyl-(1-cyclohex-3-enyloxy-2,2,6,6-tetramethyl-piperidin-4-yl)-amine, compound N, can be prepared starting from 1-cyclohex-3-enyloxy-2,2,6,6-tetramethyl-piperidin-4-yl-toluene-4-sulfonic acid. Yield: 9%; white solid.

Hydrogenation at this stage (MeOH, 5% Pd/C, 5 bar H$_2$, 40° C.) leads to butyl-(1-cyclohexyloxy-2,2,6,6-tetramethyl-piperidin-4-yl)-amine, compound D.

Flamestab NOR 116

A mixture of 6 g (8.2 mmol) of compound F, 0.47 g (2.7 mmol) N,N'-bis(3-aminopropyl)ethylenediamine and 1.7 g (8.5 mmol) aqueous 20% NaOH solution is heated in an autoclave at 125° C. for 18 h. The mixture is cooled down to 25° C., diluted with hexane and the aqueous phase split off. The organic phase is washed with water and sat. NaCl sol., dried over sodium sulfate, filtered and concentrated on a rotary evaporator. The crude oil is slowly added to boiling methanol, yielding a white precipitate. The suspension is treated with ultrasound, filtered, and the filtercake is dried to afford the product as a white powder.

The product exhibits higher quality compared to state-of-the-art material in terms of transmission and residual copper content:

|  | Transmission [%] | | |
| --- | --- | --- | --- |
|  | 425 nm | 450 nm | 500 nm |
| State of the art (Flamestab ® NOR 116; CAS-no. 191680-81-6) | 68 | 75 | 84 |
| Flamestab NOR 116 prepared via compounds C, D, F | 79 | 86 | 93 |

The amount of residual copper is below 0.1 ppm as measured by atomic absorption spectroscopy.

The invention claimed is:

1. A process for the preparation of a sterically hindered nitroxyl ether of formula (I) or (II)

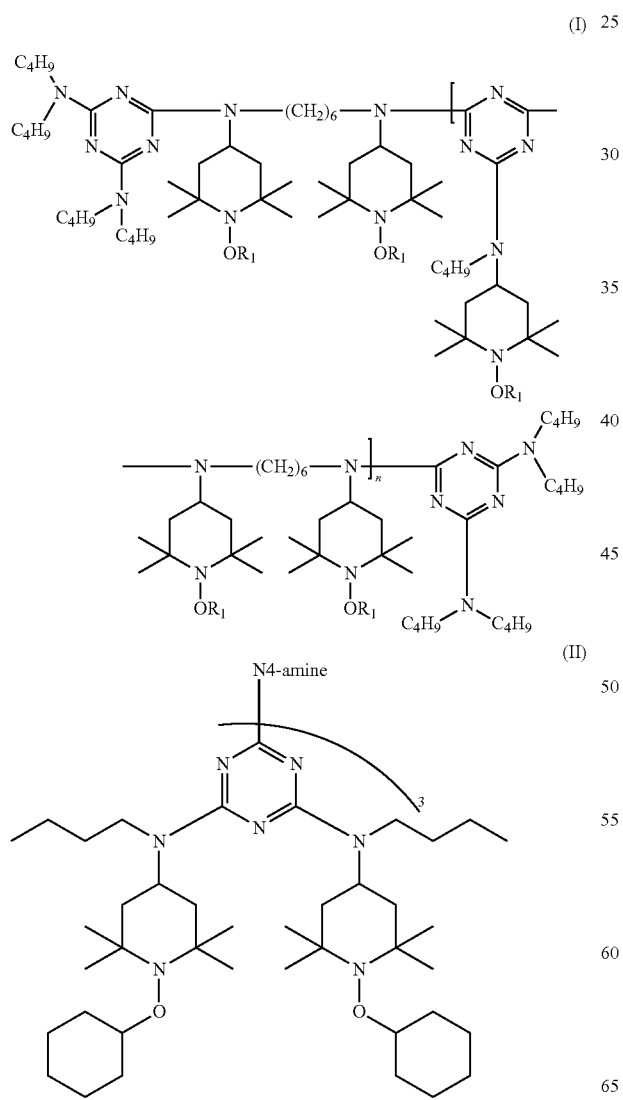

wherein
N4-amine is

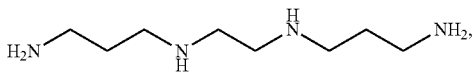

$n$ is a number from 1 to 10 and $R_1$ is $C_1$-$C_5$alkyl; which process comprises in the case of the sterically hindered nitroxyl ether of formula (I) the steps a) reacting a compound of formula (Ia)

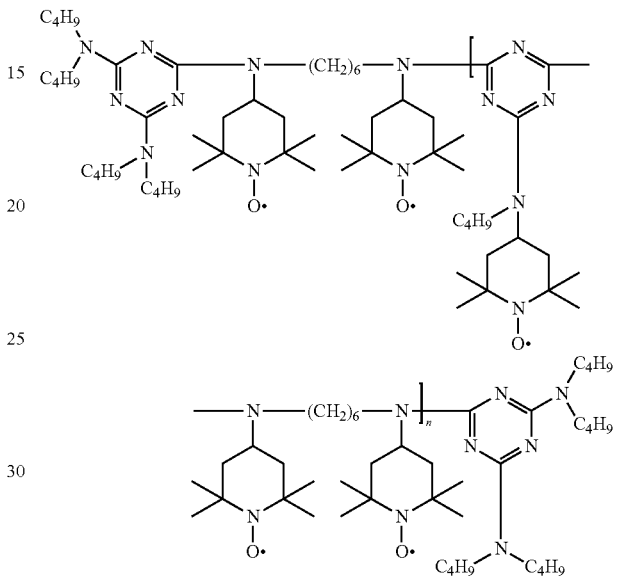

with n-hexylaldehyde, n-pentylaldehyde, n-butyraldehyde, n-propylaldehyde or acetaldehyde and a hydroperoxide in the presence of a metal catalyst; or b1) reacting a compound of formula (Ib)

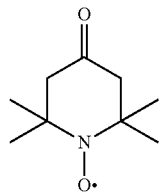

with n-hexylaldehyde, n-pentylaldehyde, n-butyraldehyde, n-propylaldehyde or acetaldehyde or a mixture of said aldehydes with their respective alcohols and a hydroperoxide in the presence of a metal catalyst to yield a compound of formula (Ic),

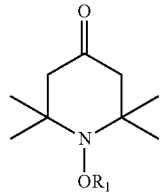

which is further reacted to form a compound of formula (I); and which process comprises in the case of the sterically hindered nitroxyl ether of formula (II)

a) reacting a compound of formula (IIa) or (IIb)

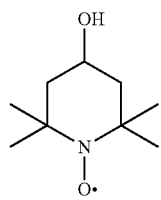
(IIa)

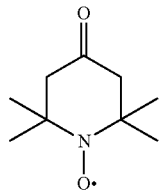
(IIb)

with a compound of formula (100) or (200)

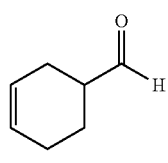
(100)

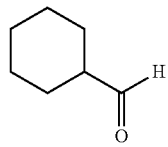
(200)

and a hydroperoxide in the presence of a metal catalyst to yield a compound of formula (IIc), (IId), (IIe) or (IIf),

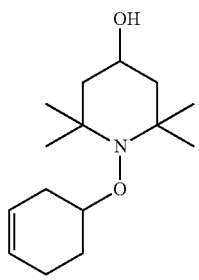
(IIc)

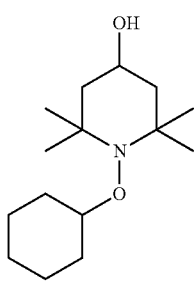
(IId)

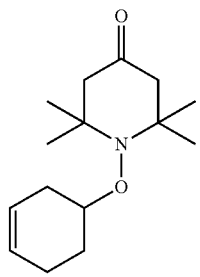
(IIe)

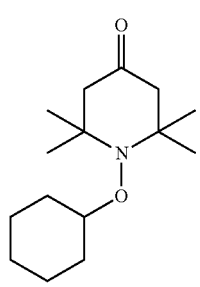
(IIf)

which are further reacted to form a compound of formula (II).

2. A process according to claim 1 wherein in formula (I) $R_1$ is n-propyl and the aldehyde is butyraldehyde.

3. A process according to claim 1 wherein the hydroperoxide is of formula (III)

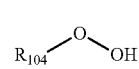
(III)

wherein $R_{104}$ is hydrogen, $C_5$-$C_{12}$cycloalkyl, $C_1$-$C_{24}$alkyl, phenyl or phenyl substituted by 1-4 $C_1$-$C_4$alkyl groups.

4. A process according to claim 1 wherein the hydroperoxide is tert-butyl hydroperoxide, cumyl hydroperoxide or $H_2O_2$.

5. A process according to claim 1 wherein the metal catalyst is a salt or a complex of Ag, Mn, Fe, Cu, Zr, Na, Mg, Ca, Al, Pd, In or Ce in any oxidation state.

6. A process according to claim 5 wherein the metal catalyst is a $Fe^{2+}$ or $Fe^{3+}$, a $Cu^+$ or $Cu^{2+}$, a $Na^+$ or a $Ca^{2+}$ salt.

7. A process according to claim 1 wherein the metal catalyst is present in an amount of 0.0005 to 10.0 molar equivalents, based on the molar equivalents of the sterically hindered nitroxyl radical.

8. A process according to claim 1 wherein the reaction is carried out at a temperature between 0° and 100° C.

9. A process according to claim 1 wherein the pH value is between 1 and 10.

10. A process for the preparation of a sterically hindered nitroxyl ether of formula (I) or (II)

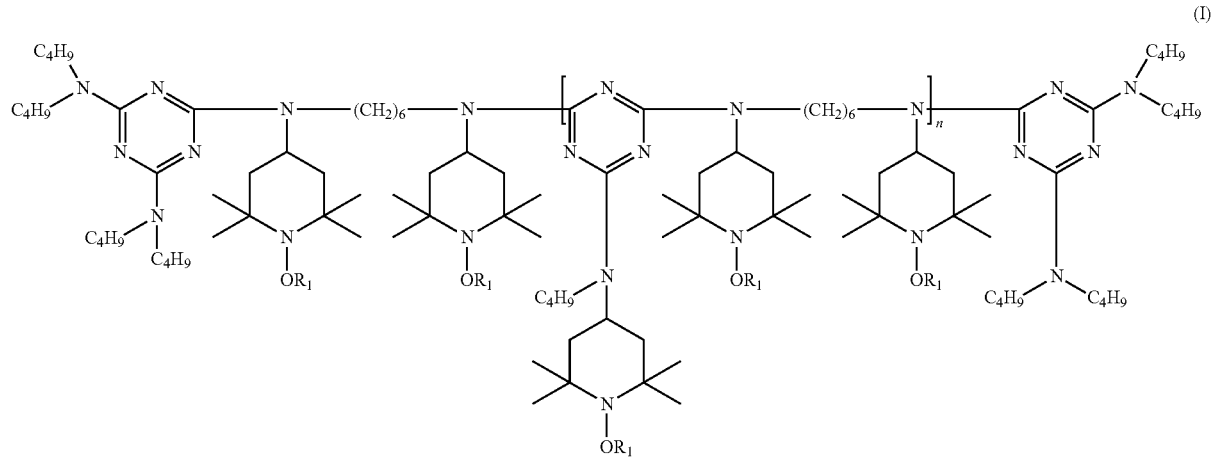
(I)
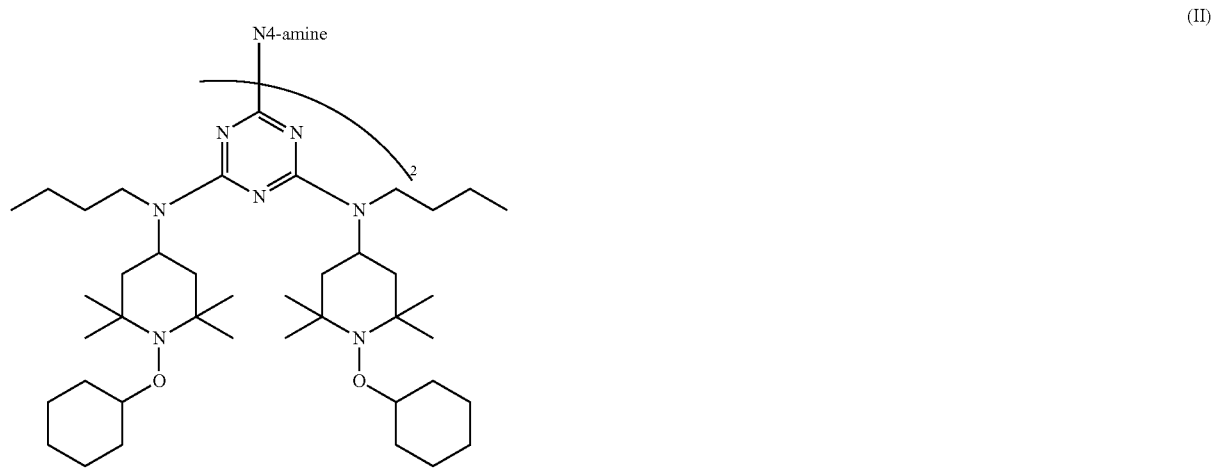
(II)
wherein
N4-amine is
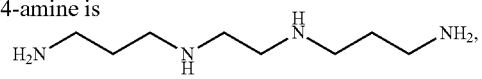
n is a number from 1 to 10 and $R_1$ is propyl; which process comprises in the case of the sterically hindered nitroxyl ether of formula (I)
a) reacting a compound of formula (Ia)
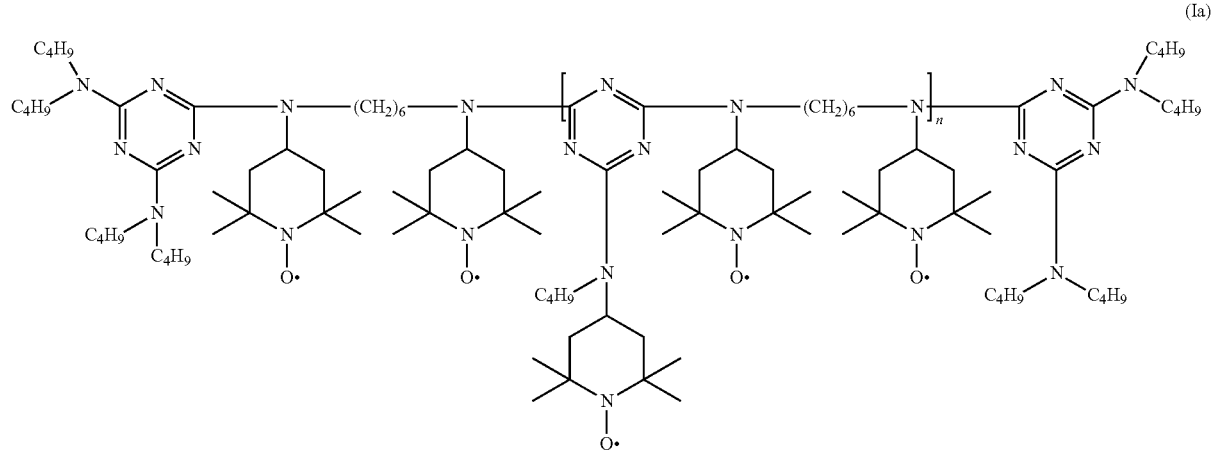
(Ia)

with n-hexylaldehyde, n-pentylaldehyde, n-butyraldehyde, n-propylaldehyde or acetaldehyde and a hydroperoxide in the presence of a metal catalyst; or b1) reacting a compound of formula (Ib)

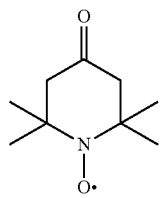
(Ib)

with n-hexylaldehyde, n-pentylaldehyde, n-butyraldehyde, n-propylaldehyde or acetaldehyde or a mixture of said aldehydes with their respective alcohols and a hydroperoxide in the presence of a metal catalyst to yield a compound of formula (Ic)

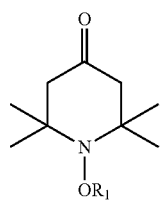
(Ic)

and b2) further reacting the compound of formula (Ic) with butylamine and subsequent hydrogenation to yield the compound of formula (Id),

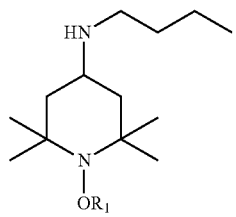
(Id)

which is reacted with cyanuric chloride to the compound of formula (Ie),

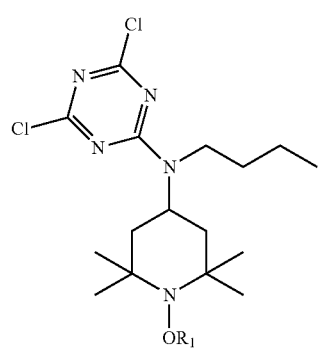
(Ie)

and reacting the compound of formula (Ic) with 1,6-diaminohexane and subsequent hydrogenation to yield the compound of formula (If),

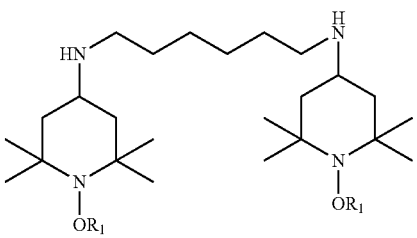
(If)

and b3) reacting the compound of formula (Ie) and (If) to yield the compound of formula (I); and which process comprises in the case of the sterically hindered nitroxyl ether of formula (II)

a) reacting a compound of formula (IIa) or (IIb),

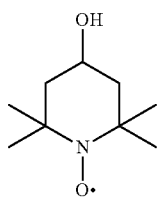
(IIa)

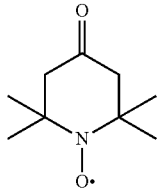
(IIb)

with a compound of formula (100) or (200),

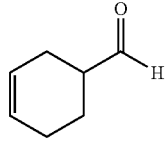
(100)

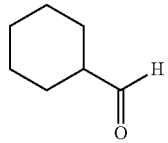
(200)

and a hydroperoxide in the presence of a metal catalyst to yield a compound of formula (IIc), (IId), (IIe) or (IIf),

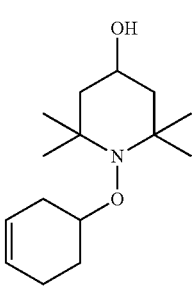
(IIc)

-continued

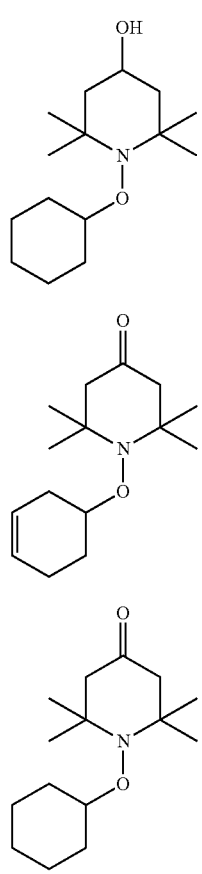

(IId)

(IIe)

(IIf)

b1) further reacting the compounds (IIe) or (IIf) directly with n-butylamine followed by hydrogenation and the compounds of formula (IIc) or (IId) after protecting the alcohol group with a protective group, with n-butylamine followed by hydrogenation to yield a compound of formula (IIg),

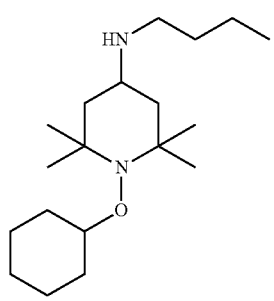

(IIg)

b2) reacting the compound of formula (IIg) with cyanuric chloride to yield the compound of formula (IIh),

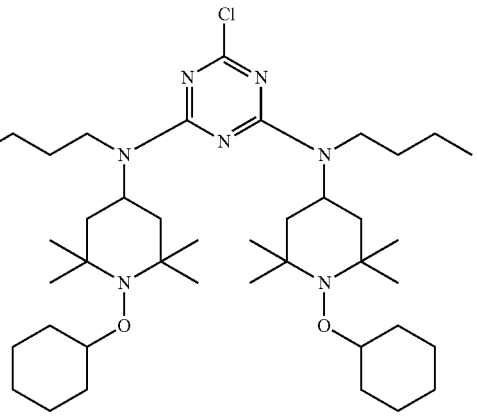

(IIh)

which is reacted with

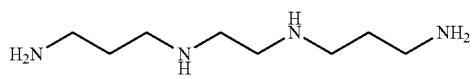 [SMILES: NCCCNCCNCCCN]

N4-amine to yield the compound of formula (II); or alternatively b3) reacting the compound of formula (IIi)

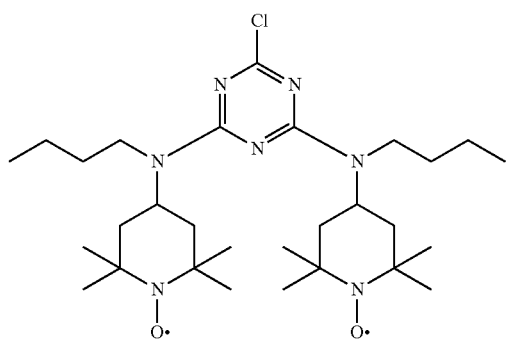

(IIi)

with compound 100 or 200 and a hydroperoxide in the presence of a metal catalyst followed by subsequent hydrogenation where appropriate to yield compound (IIh), which is further reacted with N4-amine to yield the compound of formula (II).

* * * * *